US010266903B2

(12) United States Patent
Afonina et al.

(10) Patent No.: US 10,266,903 B2
(45) Date of Patent: Apr. 23, 2019

(54) METHODS AND COMPOSITIONS FOR DETECTING ANTIBIOTIC RESISTANT BACTERIA

(71) Applicant: ELITechGroup B.V., Logan, UT (US)

(72) Inventors: Irina A. Afonina, Mill Creek, WA (US); Yevgeniy S. Belousov, Mill Creek, WA (US)

(73) Assignee: ELITECHGROUP, INC., Logan, UT (US)

( * ) Notice: Subject to any disclaimer, the term of this patent is extended or adjusted under 35 U.S.C. 154(b) by 417 days.

(21) Appl. No.: 14/957,754

(22) Filed: Dec. 3, 2015

(65) Prior Publication Data

US 2016/0168628 A1  Jun. 16, 2016

Related U.S. Application Data

(60) Provisional application No. 62/090,904, filed on Dec. 12, 2014.

(51) Int. Cl.
*C12P 19/34* (2006.01)
*C12Q 1/689* (2018.01)
*C12Q 1/6851* (2018.01)
*C12Q 1/6853* (2018.01)
*G06F 3/0488* (2013.01)
*G06Q 20/10* (2012.01)

(52) U.S. Cl.
CPC .......... *C12Q 1/689* (2013.01); *C12Q 1/6851* (2013.01); *C12Q 1/6853* (2013.01); *G06F 3/0488* (2013.01); *G06Q 20/1085* (2013.01); *C12Q 2600/158* (2013.01); *C12Q 2600/16* (2013.01)

(58) Field of Classification Search
CPC ........ C12Q 2525/161; C12Q 2561/113; C12Q 1/6851; C12Q 1/6853; C12Q 1/689; C12Q 2600/158; C12Q 2600/16; G06F 3/0488; G06Q 20/1085
USPC ....................................................... 435/91.2
See application file for complete search history.

(56) References Cited

U.S. PATENT DOCUMENTS

| 3,128,179 | A | 4/1964 | Kendall et al. |
|---|---|---|---|
| 3,194,805 | A | 7/1965 | Brooker et al. |
| 3,996,345 | A | 12/1976 | Ullman et al. |
| 4,351,760 | A | 9/1982 | Khanna et al. |
| 4,415,732 | A | 11/1983 | Caruthers et al. |
| 4,458,066 | A | 7/1984 | Caruthers et al. |
| 4,683,195 | A | 7/1987 | Mullis et al. |
| 4,739,044 | A | 4/1988 | Stabinsky |
| 4,757,141 | A | 7/1988 | Fung et al. |
| 4,965,188 | A | 10/1990 | Mullis et al. |
| 4,997,928 | A | 3/1991 | Hobbs, Jr. |
| 5,187,288 | A | 2/1993 | Kang et al. |
| 5,188,934 | A | 2/1993 | Menchen et al. |
| 5,227,487 | A | 7/1993 | Haugland et al. |
| 5,231,191 | A | 7/1993 | Woo et al. |
| 5,248,782 | A | 9/1993 | Haugland et al. |
| 5,304,645 | A | 4/1994 | Klein et al. |
| 5,419,966 | A | 5/1995 | Reed et al. |
| 5,433,896 | A | 7/1995 | Kang et al. |
| 5,442,045 | A | 8/1995 | Haugland et al. |
| 5,508,178 | A | 4/1996 | Rose et al. |
| 5,512,677 | A | 4/1996 | Chern et al. |
| 5,538,848 | A | 7/1996 | Livak et al. |
| 5,556,959 | A | 9/1996 | Brush et al. |
| 5,583,236 | A | 12/1996 | Brush |
| 5,585,481 | A | 12/1996 | Arnold, Jr. et al. |
| 5,696,251 | A | 12/1997 | Arnold, Jr. et al. |
| 5,736,626 | A | 4/1998 | Mullah et al. |
| 5,801,155 | A | 9/1998 | Kutyavin et al. |
| 5,808,044 | A | 9/1998 | Brush et al. |
| 5,852,191 | A | 12/1998 | Karandikar et al. |
| 5,905,848 | A | 5/1999 | Yano et al. |
| 5,925,517 | A | 7/1999 | Tyagi et al. |
| 5,942,610 | A | 8/1999 | Nelson et al. |
| 5,986,086 | A | 11/1999 | Brush et al. |
| 5,994,056 | A | 11/1999 | Higuchi |
| 6,020,481 | A | 2/2000 | Benson et al. |
| 6,127,121 | A | 10/2000 | Meyer, Jr. et al. |
| 6,162,931 | A | 12/2000 | Gee et al. |

(Continued)

FOREIGN PATENT DOCUMENTS

EP   1408366 A2   4/2004
WO   99/37805 A1  7/1999

(Continued)

OTHER PUBLICATIONS

Afonina et al. Biotechnique, 43 (6), 770-773 (Year: 2007).*

(Continued)

*Primary Examiner* — Cynthia B Wilder

(74) *Attorney, Agent, or Firm* — Jackson Walker LLP

(57) ABSTRACT

Primers and probes specific to the genes encoding extended spectrum beta-lactamase that involves CTX-M groups 1 and 9 that cause extended beta-lactamase resistance in bacteria are described herein, with methods and kits for using these primers and probes to detect CTX-M groups 1 and 9 nucleic acids. In the methods described, nucleic acids present in a clinical or test sample obtained from a biological sample or tissue suspected of containing the CTX-M groups 1 and 9 gene are amplified and corresponding sequences for CTX-M groups 1 and 9 are detected. The amplified nucleic acid can be detected by a variety of state of the art methods, including fluorescence resonance energy transfer (FRET), radiolabels, enzyme labels, and the like.

28 Claims, 3 Drawing Sheets

Specification includes a Sequence Listing.

(56) References Cited

U.S. PATENT DOCUMENTS

| | | | |
|---|---|---|---|
| 6,180,295 B1 | 1/2001 | Helber et al. | |
| 6,221,604 B1 | 4/2001 | Upadhya et al. | |
| 6,312,894 B1 | 11/2001 | Hedgpeth et al. | |
| 6,653,473 B2 | 11/2003 | Reed et al. | |
| 6,683,173 B2 | 1/2004 | Dempcy et al. | |
| 6,699,975 B2 | 3/2004 | Reed et al. | |
| 6,727,356 B1 | 4/2004 | Reed et al. | |
| 6,790,945 B2 | 9/2004 | Lukhtanov et al. | |
| 6,949,367 B1 | 9/2005 | Dempcy et al. | |
| 6,972,339 B2 | 12/2005 | Lukhtanov et al. | |
| 7,045,610 B2 | 5/2006 | Dempcy et al. | |
| 7,205,105 B2 | 4/2007 | Afonina et al. | |
| 7,319,022 B1 | 1/2008 | Mahoney et al. | |
| 7,381,818 B2 | 6/2008 | Lokhov et al. | |
| 7,582,739 B2 | 9/2009 | Lukhtanov et al. | |
| 7,662,942 B2 | 2/2010 | Reed et al. | |
| 7,671,218 B2 | 3/2010 | Lukhtanov et al. | |
| 7,759,126 B2 | 7/2010 | Lokhov et al. | |
| 7,767,834 B2 | 8/2010 | Lukhtanov et al. | |
| 7,790,385 B2 | 9/2010 | Kutyavin et al. | |
| 7,968,292 B2 | 6/2011 | Whiteford et al. | |
| 8,163,910 B2 | 4/2012 | Lukhtanov | |
| 8,410,255 B2 | 4/2013 | Cook et al. | |
| 2005/0118623 A1 | 6/2005 | Belousov et al. | |
| 2007/0048758 A1 | 3/2007 | Lokhov et al. | |
| 2007/0248954 A1 | 10/2007 | Hanson | |
| 2009/0031780 A1 | 2/2009 | Bandou et al. | |
| 2009/0163382 A1* | 6/2009 | Oh | C12Q 1/689 506/17 |
| 2011/0190170 A1 | 8/2011 | Sampath et al. | |
| 2012/0129180 A1 | 5/2012 | Kirveskari et al. | |
| 2012/0244535 A1 | 9/2012 | Vorobiev et al. | |
| 2012/0245219 A1 | 9/2012 | Khvorova et al. | |
| 2013/0065790 A1* | 3/2013 | Vos | C12Q 1/689 506/9 |
| 2013/0261014 A1 | 10/2013 | Vorobiev et al. | |

FOREIGN PATENT DOCUMENTS

| | | | |
|---|---|---|---|
| WO | 2001/042505 A2 | 6/2001 | |
| WO | 2003/023357 A2 | 3/2003 | |
| WO | 2010/096723 A1 | 8/2010 | |
| WO | 2011/138402 A1 | 11/2011 | |
| WO | 2012/023054 A3 | 2/2012 | |
| WO | 2012/032158 A1 | 3/2012 | |
| WO | WO 2012032158 | * | 3/2012 |
| WO | 2013/078565 A1 | 6/2013 | |
| WO | 2014/008312 A2 | 1/2014 | |
| WO | WO 2015018980 | * | 12/2015 |

OTHER PUBLICATIONS

Genbank accession No. AY515297.1 (Genbank I) (https://www.ncbi.nlm.nih.gov/nuccore/AY515297, Dec. (Year: 2005).*

Genbank accession No. JQ235792 (Genbank II) (https://www.ncbi.nlm.nih.gov/nuccore/JQ235792, Mar. (Year: 2012).*

Bengtsson et al., "A New Minor Groove Binding Asymmetric Cyanine Report Dye for Real-Time PCR", Nucleic Acids Research, 2003, pp. 1-5, vol. 31, No. 8, e45.

Bolli et al., "Watson-Crick Base-Paring Properties of Bicyclo-DNA", Nucleic Acids Research, 1996, pp. 4660-4667, vol. 24, No. 23.

Bonnet, "Growing Group of Extended-Spectrum β-Lactamases: the CTX-M Enzymes", Antimicrobial Agents and Chemotherapy, 2004, pp. 1-14, vol. 48, No. 1.

Capaldi et al., "Signal Amplification Through Nucleotide Extension and Excision on a Dendritic DNA Platform", Nucleic Acids Research, 2000, pp. 1-8, vol. 28, No. 7, e21.

Dallenne et al., "Development of a set of multiplex PCR assays for the detection of genes encoding important β-actamases in Enterobacteriaceae", Journal of Antimicrobial Chemotherapy, 2010, pp. 490-495, vol. 65. No. 3.

Dreier et al., "Use of Bacteriophage MS2 as an Internal Control in Viral Reverse Transcroption-PCR Assays", Journal of Clinical Microbiology, 2005, pp. 4551-4557, vol. 43, No. 9.

Brown et al., "Modern Machine-aided methods of oligodeoxyribonucleotide synthesis", Oligonucleotides and Analogues: A Practical Approach, IRL Press, 1991, pp. 1-25.

Garrido et al., "Characterization of plasmid-mediated β-lactamases in fecal colonizing patients in the hospital and community setting in Spain", Microbial Drug Resistance, 2014, pp. 301-304, vol. 20, No. 4.

Georgopapadakou, "Prospects for New Antibacterials; Can We Do Better?", Expert Opinion Investig. Drugs, 2014, pp. 145-148, vol. 23, No. 2.

Giusti et al., "Synthesis and characterization of 5'-fluorescent-dye-labeled oligonucleotides", PCR Methods and Applications, Genome Research, 1993, pp. 223-227, vol. 2.

Hawkey et al., "The changing epidemiology of resistance", Journal of Antimicrobial Chemotherapy, 2009, pp. i3-10, vol. 64, Suppln 1.

Hoorfar et al., "Practical Considerations in Design of Internal Amplification Controls for Diagnostic PCR Assays," Journal of Clinical Microbiology, 2004, pp. 1863-1868, vol. 42, No. 5.

Helldal et al., "Shift of CTX-M genotypes has determined the increased prevalence of extended-spectrum β-lactamase-producing *Escherichia coli* in south-western Sweden", Clinical Microbiology and Infection, 2013, pp. E87-E90, vol. 19.

Kutyavin et al., 3'-Minor Groove Binder-DNA Probes Increase Sequence Specificity at PCR Extension Temperatures, Nucleic Acids Research, 2000, pp. 655-661, vol. 28, No. 2.

Leistner et al., "Mortality and molecular epidemiology associated with extended-spectrum β-lactamase production in *Escherichia coli* from bloodstream infection", Infection and Drug Resistance, 2014, pp. 57-62, vol. 7.

Mullis et al., "Specific Enzymatic Amplification of DNA In Vitro: The Polymerase Chain Reaction", Cold Spring Harb. Symp. Quant. Biol., 1986, pp. 263-273, vol. 51.

Nelson et al., "Bifunctional Oligonucleotide Probes Synthesized Using a Novel CPG Support are able to Detect Single Base Pair Mutations", Nucleic Acids Research, 1989. pp. 7187-7194, vol. 17, No. 18.

Niemz et al., "Point-of-care Nucleic Acid Testing for Infectious Diseases", Trends in Biotechnology, 2011, pp. 240-250, vol. 29, No. 5.

Papagiannitsis et al., "Characterization of Metallo-β-Lactamase VIM-27, an A57S Mutant of VIM-1 Associated with Klebsiella pneumoniae ST147", Antimicrobial Agents and Chemotherapy, 2011, pp. 3570-3572, vol. 55, No. 7.

Perez et al., "Carbapenem-resistant Enterobacteriaceae: A Menace to our most vulnerable patients", Cleveland Clinic Journal of Medicone, 2013, pp. 225-233, vol. 80, No. 4.

Picard et al., "Internal control for nucleic acid testing based on the use of purified *Bacillus atrophaeus* subsp. *globigii* spores", Journal of Clinical Microbiology, 2009, pp. 751-757, vol. 47, No. 3.

Poirel et al., "Emergence of Oxacillinase-Mediated Resistance to Imipenem in Klebsiella pneumoniae", Antimicrobial Agents and Chemotherapy, 2004, pp. 15-22, vol. 48, No. 1.

Potron et al., "Characterization of OXA-181, a Carbapenem-Hydrolyzing Class D β-Lactamase from Klebsiella pneumoniae" Antimicrobial Agents and Chemotherapy, 2011, pp. 4896-4899, vol. 55, No. 10.

Sambrook et al., "Molecular Cloning: A Laboratory Manual" Cold Spring Harbor Laboratory Press, 1989,pp. 1-21.

Samuelsen et al., "Identification of Enterobacteriaceae isolates with OXA-48 and coproduction of OXA-181 and NDM-1 in Norway", J Antimicrob Chemother., 2013, pp. 1682-1685, vol. 68, No. 7.

Sharma et al., "A general method for the synthesis of 3'-sulfhydryl and phosphate group containing oligonucleotides", Nuc. Acids Res., 1991, pp. 3019-3025, vol. 19, No. 11.

Sproat et al. "The synthesis of protected 5'-mercapto-2', 5'-dideoxyribonucleoside-3'-0-phosphorainidites; uses of 5'-mercapto-oligodeoxyribonucleotides", Nucleic Acids Research, 1987, pp. 4837-4848, vol. 15, No. 12.

(56) References Cited

OTHER PUBLICATIONS

Yigit et al., "Novel Carbapenem-Hydrolyzing β-Lactamase, KPC-1, from a Carbapenem-Resistant Strain of Klebsiella pneumoniae" Antimicrobial Agents and Chemotherapy, 2001, pp. 1151-1161, vol. 45, No. 4.

Yong et al., "Characterization of a New Metallo-β-Lactamase Gene, blaNDM-1, and a Novel Erythromycin Esterase Gene Carried on a Unique Genetic Structure in Klebsiella pneumoniae Sequence Type 14 from India" Antimicrobial Agents and Chemotherapy, 2009, pp. 5046-5054, vol. 53, No. 12.

Zuckermann et al., "Efficient methods for attachment of thiol specific probes to the 3'-ends of synthetic oligodeoxyribonucleotides", Nucleice Acids Research, 1987, pp. 5305-5321, vol. 15, No. 13.

The International Preliminary Report on Patentability issued by the International Bureau of WIPO dated Jun. 22, 2017 for International PCT application No. PCT/US2015/063614.

The International Search Report and the Written Opinion issued by European Patent Office dated Mar. 14, 2016 for International PCT Application No. PCT/US2015/063614.

Afonina et al., "Primers with 5' flaps improve real-time PCR", BioTechniques, 2007, pp. 770-774, vol. 43, No. 6.

Parveen et al., "Study of CTX-M Type of Extended Spectrum β-Lactamase among Nosocomial Isolates of *Escherichia coli* and Klebsiella pneumoniae in South India", Indian J. Microbiol., 2012, pp. 35-40, vol. 52, No. 1.

Wang et al., "Transposition of ISEcp1 modulates blaCTX-M-55-mediated Shigella flexneri resistance to cefalothin", International Journal of Antimicrobial Agents, 2013, pp. 507-512, vol. 42, No. 6.

Afonina et al., "Hybridization-triggered Fluorescence detection of DNA with minor groove binder-conjugated Probes", Medical Imaging, 2002, pp. 326-329, vol. 4626.

\* cited by examiner

METHODS AND COMPOSITIONS FOR DETECTING ANTIBIOTIC RESISTANT BACTERIA

This application claims priority to U.S. Provisional Patent Application Ser. No. 62/090,904, entitled "Methods and Compositions for Detecting Antibiotic Resistant Bacteria," filed on Dec. 12, 2014, the entire content of which is hereby incorporated by reference.

BACKGROUND

This disclosure relates to bacterial diagnostics, and more particularly to methods and compositions for detecting antibiotic resistant bacteria using preferred primers, probes, and assays directed to genes encoding extended spectrum beta-lactamase.

β-Lactam antibiotics (beta-lactam antibiotics) are a broad class of antibiotics, consisting of all antibiotic agents that contain a β-lactam ring in their molecular structures. This includes penicillin derivatives (penams), cephalosporins (cephems), monobactams and carbapenems. (Holten K B 2000). Most β-lactam antibiotics work by inhibiting cell wall biosynthesis in the bacterial organism and are the most widely used group of antibiotics. β-Lactam antibiotics are indicated for the prophylaxis and treatment of bacterial infections caused by susceptible organisms. At first, β-lactam antibiotics were mainly active only against Gram-positive bacteria, yet the recently developed broad-spectrum β-lactam antibiotics are active against various Gram-negative organisms, which has increased their usefulness.

The production of β-lactamases is the predominant cause of resistance to β-lactam antibiotics in gram-negative bacteria. The CTX-M beta-lactamases enzymes were named for their greater activity against cefotaxime. Evolution of multidrug resistant (MDR) bacteria under the pressure of excessive antibiotic use with horizontal gene transfer provide the means by which genes such as bla(CTX-M) spread amongst different bacterial species and strains (Hawkey P M 2009, Liebana et al. 2013). More than 80 CTX-M enzymes are currently known. CTX-M1-, and CTX-M9-groups represent five and nine closely related enzymes, respectively, and are particularly clinically relevant (Garrido et al. 2014; Helldal et al. 2013; Onnberg et al. 2011; Dallenne et al. 2010). CTX-M enzymes are observed in different members of the family Enterobacteriaceae which include, among others, *Salmonella* and *E. coli*. Typically the blaCTX-M gene is located on transferable plasmids of different sizes and structures, with the group 1 and 9, respectively, 97 and 98% similar (Bonnet 2004). The specific detection of clinical relevant groups 1 and 9 in the background of less clinical relevant CTX-M groups present special challenges.

There exists a clinical need for the rapid detection of the carriers of antibiotic resistant β-lactamase genes among which the CTX-M1 and CTX-M9 groups have higher clinical prevalence rates.

SUMMARY

The present disclosure relates to primers and probes specific to the genes encoding extended spectrum beta-lactamase that involves CTX-M groups 1 and 9 that cause extended beta-lactamase resistance in bacteria.

More specifically, the present disclosure relates to primers and probes for the detection of genes encoding certain beta-lactamases in samples including biological samples (e.g., rectal swabs). The present invention discloses primers and probes to identify the family of specific beta lactamases producers that carry antibiotic resistance genetic markers in clinical isolates of preferably gram negative bacteria. Specific primers and probes to amplify and detect resistance-encoding genes that involve CTX-M groups 1 and 9 are disclosed in the primer and probe sequences herein. In the methods described, nucleic acids present in a clinical or test sample obtained from a biological sample or tissue suspected of containing the CTX-M groups 1 and 9 gene are amplified and corresponding sequences for CTX-M groups 1 and 9 are detected. The amplified nucleic acid can be detected by a variety of state of the art methods, including fluorescence resonance energy transfer (FRET), radiolabels, enzyme labels, and the like. The amplified nucleic acids can also be detected by any combination of detection techniques which may include hybridization detection probes.

One embodiment pertains to a method for detecting CTX-M groups 1 and 9 in a biological sample from an individual. Other embodiments provide oligonucleotide primers and probes comprising nucleotide sequences characteristic of CTX-M groups 1 and 9 gene sequences. The method includes performing at least one cycling step of amplification and hybridization. The amplification step includes contacting the sample nucleic acid with one or more pairs of primers to produce amplification product if the CTX-M groups 1 and 9 nucleic acid is present. The preferred primers target specific regions of the CTX-M gene of a resistant organism. The oligonucleotide probes detect the amplified target directly or indirectly. The most preferred oligonucleotide probe is a 5'-minor groove binder-fluorophore-oligonucleotide-quencher-3' conjugate that fluoresces on hybridization to its complementary amplified target. In another embodiment the preferred oligonucleotide probe is a 3'-minor groove binder-quencher-oligonucleotide-fluorophore-3' conjugate that fluoresces on hybridization to its complementary amplified target when cleaved by 5'-endonuclease activity.

Kits are also provided for the detection of CTX-M groups 1 and 9 genes in biological samples comprising at least one annealing oligonucleotide primer reagent specific for the amplification of CTX-M groups 1 and 9 sequences and comprising at least one oligonucleotide probe specific for the detection of CTX-M groups 1 and 9 sequences.

The method further includes detecting of the presence or absence of a fluorescent signal (e.g., a signal resulting from FRET) of the hybridization probe of the invention. The presence of the fluorescent signal usually indicates the presence of CTX-M groups 1 and 9 gene sequences in the biological sample, while the absence of signal usually indicates the absence of CTX-M groups 1 and 9 gene sequences in the biological sample.

The method can additionally include determining the melting temperature profile between the probe and the amplification product. The melting curve further confirms the presence or absence of CTX-M groups 1 and 9 gene sequences and potential presence of CTX-M groups 1 and 9 gene sequences, with mismatch(es) in the probe sequence area.

The primers and probes of the invention allow the specific, sensitive, and rapid detection of CTX-M groups 1 and 9 gene sequences that have higher clinical prevalence rates.

DETAILED DESCRIPTION

I. General

Figure 1:
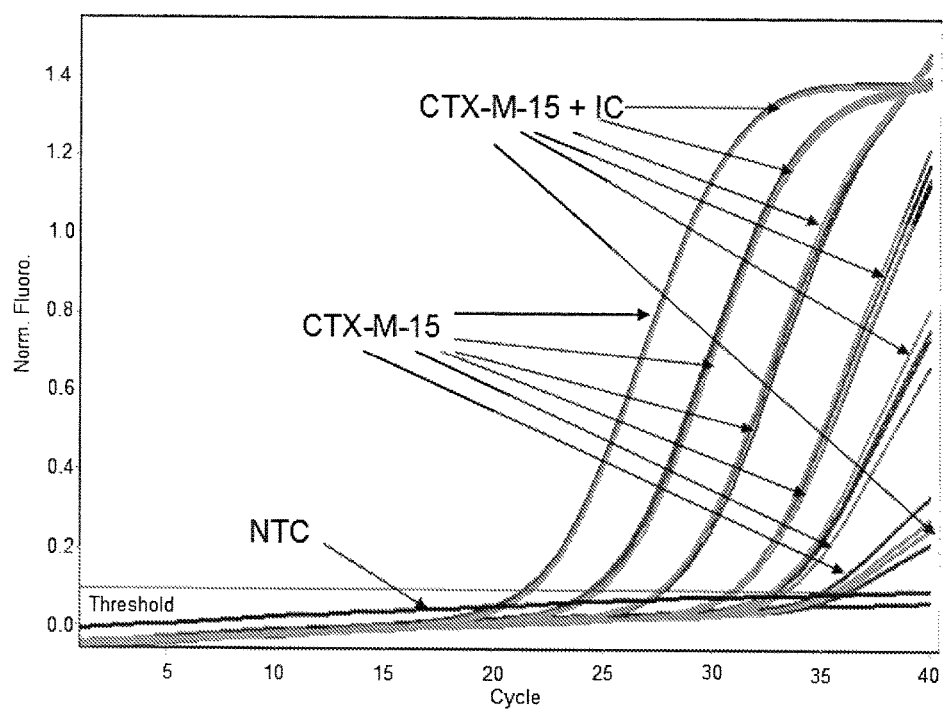
FIG. 1 shows real-time titration (tenfold titration (100 pg-1 fg)) of CTX-M15 DNA extracted from *E. coli* ATCC BAA-2326 alone and with Internal Control.

The present disclosure provides primers and probes for use in methods for the specific amplification and/or detection of nucleic acid sequences encoding certain beta-lactamases, namely CTX-M groups 1 and 9.

II. Definitions

The term "CTX-M" as used herein refers to Extended-Spectrum β-Lactamases causing antibiotic resistance in mainly gram negative bacteria that acquired chromosomal bla$_{CTX-M}$ related genes from different species of *Kluyvera*. The CTX-M-1 group includes six plasmid-mediated enzymes (CTX-M-1, CTX-M-3, CTX-M-10, CTX-M-12, CTX-M-15, and FEC-1) showing >97% identity and CTX-M-9 group includes nine plasmid-mediated enzymes (CTX-M-9, CTX-M-13. CTX-M-14, CTX-M-16, CTX-M-17, CTX-M-19, CTX-M-21, CTX-M-27, and Toho-2) (Bonnet 2004) showing >98% identity.

A "sample" as used herein refers to a sample of any source which is suspected of containing CTX-M nucleic acids. These samples can be tested by the methods described herein. A sample can be from a laboratory source or from a non-laboratory source. A sample may be suspended or dissolved in liquid materials such as buffers, extractants, solvents, and the like. Samples also include biological samples such as animal and human tissue or fluids such as whole blood, blood fractions, serum, plasma, cerebrospinal fluid, lymph fluids, milk, urine, various external secretions of the respiratory, intestinal, and genitourinary tracts, tears, and saliva; and biological fluids such as cell extracts, cell culture supernatants, fixed tissue specimens, and fixed cell specimens. Samples include nasopharyngeal or throat swabs, stools, or rectal swabs. Biological samples may also include sections of tissues such as biopsy and autopsy samples or frozen sections taken for histologic purposes. A biological sample is obtained from any mammal including, e.g., a human.

The terms "flap primer" or "overhang primer" refer to a primer comprising a 5' sequence segment non-complementary to a target nucleic acid sequence (e.g., a CTX-M groups 1 and 9 nucleic acid sequence) and a 3' sequence segment complementary to the target nucleic acid sequence (e.g., a CTX-M groups 1 and 9 nucleic acid sequence). The flap primers of the invention are suitable for primer extension or amplification of the target nucleic acid sequence (e.g., CTX-M groups 1 and 9 nucleic acid sequence).

The term "overhang sequence" refers to a non-complementary adapter, flap, or overhang sequence in a primer. "Non-complementary" sequences do not bind to a target sequence under amplification conditions. The flap portion of a flap primer can comprise nucleotides that are complementary to the target sequence provided that the three nucleotides immediately 5' to the portion of the flap are not complementary to the target sequence.

The term "fluorescent generation probe" refers either to a) an oligonucleotide having an attached minor groove binder, fluorophore, and quencher or b) a DNA binding reagent. The probes may comprise one or more non-complementary or modified nucleotides (e.g., pyrazolopyrimidines as described herein below) at any position including, e.g., the 5' end. In some embodiments, the fluorophore is attached to the modified nucleotide.

The term "modified bases" refers to those bases that differ from the naturally-occurring bases (adenine, cytosine, guanine, thymine, and urasil) by addition or deletion of one or more functional groups, differences in the heterocyclic ring structure (i.e., substitution of carbon for a heteroatom, or vice versa), and/or attachment of one or more linker arm structures to the base. Preferred modified nucleotides are those based on a pyrimidine structure or a purine structure, with the latter more preferably being 7 deazapurines and their derivatives and pyrazolopyrimidines (described in U.S. Pat. No. 7,045,610); and also described in U.S. Pat. No. 6,127,121. Preferred modified bases are 5-substituted pyrimidines and 3-substituted pyrazolopyrimidines. Examples of preferred modified bases are 6-amino-1H-pyrazolo[3,4-d]pyrimidin-4(5H)-one (PPG or Super G®), 4-amino-1H-pyrazolo[3,4-d]pyrimidine, 1H-pyrazolo[5,4-d]pyrimidin-4(5H)-6(7H)-dione, 6-amino-3-prop-1-ynyl-5-hydropyrazolo[3,4-d]pyrimidine-4-one, 6-amino-3-(3-hydroxyprop-1-yny)l-5-hydropyrazolo[3,4-d]pyrimidine-4-one, 6-amino-3-(3-aminoprop-1-ynyl)-5-hydropyrazolo[3,4-d]pyrimidine-4-one, 4-amino-3-(prop-1-ynyl)pyrazolo[3,4-d]pyrimidine, 4-amino-3-(3-hydroxyprop-1-ynyl)pyrazolo[3,4-d]pyrimidine, 4-amino-3-(3-aminoprop-1-ynyl)pyrazolo[3,4-d]pyrimidine, 3-prop-1-ynyl-4,6-diaminopyrazolo[3,4-d]pyrimidine. 2-(4,6-diaminopyrazolo[3,4-d]pyrimidin-3-yl)ethyn-1-ol, 3-(2-aminoethynyl)pyrazolo[3,4-d]pyrimidine-4,6-diamine, 5-prop-1-ynyl-1,3-dihydropyrimidine-2,4-dione, 5-(3-hydroxyprop-1-ynyl)-1,3-dihydropyrimidine-2,4-dione, 6-amino-5-prop-1-ynyl-3-dihydropyrimidine-2-one, 6-amino-5-(3-hydroxyprop-1-yny)-1,3-dihydropyrimidine-2-one, 6-amino-5-(3-aminoprop-1-yny)-1,3-dihydropyrimidine-2-one, 5-[4-amino-3-(3-methoxyprop-1-ynyl)pyrazol[3,4-d]pyrimidinyl]-2-(hydroxymethyl)oxolan-3-ol, 6-amino-1-[4-hydroxy-5-(hydroxymethyl)oxolan-2-yl]-3-(3-methoxyprop-1-ynyl)-5-hydropyrazolo[3,4-d]pyrimidin-4-one, 4-(4,6-Diamino-1H-pyrazolo[3,4-d]pyrimidin-3-yl)-but-3-yn-1-ol (Super A®), 6-Amino-3-(4-hydroxy-but-1-ynyl)-1,5-dihydro-pyrazolo[3,4-d]pyrimidin-4-one, 5-(4-hydroxy-but-1-ynyl)-1H-pyrimidine-2,4-dione (Super T®), 3-iodo-1H-pyrazolo[3,4-d]pyrimidine-4,6-diamine, 3-bromo-1H-pyrazolo[3,4-d]pyrimidine-4,6-diamine, 3-chloro-1H-pyrazolo[3,4-d]pyrimidine-4,6-diamine, 3-Iodo-1H-pyrazolo[3,4-d]pyrimidin-4-ylamine, 3-Bromo-1H-pyrazolo[3,4-d]pyrimidin-4-ylamine and 3-chloro-1H-pyrazolo[3,4-d]pyrimidin-4-ylamine. Examples of universal bases can be find co-owned U.S. Application US2013/0261014 incorporated by reference herein.

The terms "fluorescent label" or "fluorophore" refer to compounds with a fluorescent emission maximum between about 400 and about 900 nm. These compounds include, with their emission maxima in nm in brackets, Cy2™ (506), GFP (Red Shifted) (507), YO-PRO™-1 (509), YOYO™-1 (509), Calcein (517), FITC (518), FluorX™ (519), Alexa™ (520), Rhodamine 110 (520), 5-FAM (522), Oregon Green™ 500 (522?, Oregon Green™ 488 (524), RiboGreen™ (525). Rhodamine Green™ (527), Rhodamine 123 (529), Magnesium Green™ (531), Calcium Green™ (533), TO-PRO™-1 (533), TOTO®-1 (533). JOE (548), BODIPY® 530/550 (550), DiI (565), BODIPY® 558/568 (568), BODIPY® 564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamnine B (580), TAMRA (582), Rhodamine Red™ (590), Cy3.5™ (596), ROX (608), Calcium Crimson™ (615), Alexa™ 594 (615), Texas Red™ (615), Nile Red (628), YO-PRO™-3 (631), YOYO™-3 (631), R-phycocyanin (642), C-Phycocyanin (648), TO-PRO™-3 (660), TOTO™-3 (660), DiD DiIC(5) (665), Cy5™ (670), Thiadicarbocyanine (671), and Cy5.5 (694). Additional fluorophores are disclosed in PCT Patent Publication No. WO 03/023357 and U.S. Pat. No. 7,671, 218. Examples of these and other suitable dye classes can be found in Haugland et al., Handbook of Fluorescent Probes and Research Chemicals, Sixth Ed., Molecular Probes, Eugene, Ore. (1996); U.S. Pat. Nos. 3,194,805; 3,128,179; 5,187,288; 5,188,934; 5,227,487; 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP Patent No. 1408366; Still other dyes are provided via online sites such as zeiss.com. Phosphonate dyes are disclosed in co-owned U.S. Pat. No. 7,671,218, U.S. Pat. Nos. 7,767,834 and 8,163,910.

There is extensive guidance in the art for selecting quencher and fluorophore pairs and their attachment to oligonucleotides (Haugland, 1996; U.S. Pat. Nos. 3,996,345, 4,351,760 and 8,410,255 and the like).

Preferred quenchers are described in co-owned U.S. Pat. Nos. 6,727,356 and 7,662,942.

In the description herein, the abbreviations M, FL, Q, CPG, and ODN refer to "minor groove binder," "fluorescent label" or "fluorophore," "quencher," "controlled pore glass" (as an example of a solid support), and "oligonucleotide" moieties or molecules, respectively, and in a manner which is apparent from context. The terms "probe" and "conjugate" are used interchangeably and preferably refer to an oligonucleotide having an attached minor groove binder, fluorophore, and quencher.

The terms "oligonucleotide," "nucleic acid," and "polynucleotide" are used interchangeably herein. These terms refer to a compound comprising nucleic acid, nucleotide, or its polymer in either single- or double-stranded form, e.g., DNA, RNA, analogs of natural nucleotides, and hybrids thereof. The terms encompass polymers containing modified or non-naturally-occurring nucleotides, or to any other type of polymer capable of stable base-pairing to DNA or RNA including, but not limited to, peptide nucleic acids as described in Nielsen et al., Science, 254:1497-1500 (1991), bicyclo DNA oligomers as described in Bolli et al., Nucleic Acids Res., 24:4660-4667 (1996), and related structures. Unless otherwise limited, the terms encompass known analogs of natural nucleotides that hybridize to nucleic acids in a manner similar to naturally-occurring nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs) and any combination thereof. A "subsequence" or "segment" refers to a sequence of nucleotides that comprise a part of a longer sequence of nucleotides.

The term "internal control" refers to a control amplification reaction that monitors false negative amplification of targets due to failure of one or more reagents, failure of amplification due to thermal cycling, inhibition of amplification, failure of reporting the reaction, or similar failures. The use of Bacteriophage MS2 (Dreier 2005) and purified *Bacillus atrophaeus* subsp. *globigii* spores as internal controls (Picard 2009) have been reported. Practical considerations in design of competitive and non-competitive internal controls are also known in the field (Hoorfar 2004).

The practice of the methods described herein will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996); Gait (ed.), OLIGONUCLEOTIDE SYNTHESIS: A PRACTICAL APPROACH, IRL Press (1984); and Eckstein (ed.), OLIGONUCLEOTIDES AND ANALOGUES: A PRACTICAL APPROACH, IRL Press (1991).

III. Description

Preferred embodiments herein are directed to primers and probes for use in methods for specific amplifying and/or detecting CTX-M groups 1 and 9 nucleic acids. Primers and probes of the invention are suitable to be used in the methods of the invention to detect CTX-M groups 1 and 9 sequences either simultaneously in a single reaction or in separate reactions. Typically, the amplification methods are performed on CTX-M groups 1 and 9 nucleic acids. One such amplification method is the polymerase chain reaction (see, e.g., U.S. Pat. Nos. 4,683,195 and 4,965,188; Mullis et al., *Cold Spring Harb. Symp. Quant. Biol.*, 51 Pt 1:263-273 (1986)).

Amplification procedures are those in which many copies of a target nucleic acid sequence are generated, usually in an exponential fashion, by sequential polymerization and/or ligation reactions. In addition to the more traditional amplification reactions discussed below, the present method is useful in amplifications involving three-way junctures (see, e.g., WO 99/37085), signal amplification (see, e.g., Capaldi, et al., Nuc. Acids Res., 28:E21 (2000)), T7 polymerases, reverse transcriptase, RNase H, RT-PCR, Rolling Circles, cleavase and the like. Isothermal amplification methods have been reviewed (Niemz, A. et al Trends Biotechnol., 29: 240-50 (2011)). The term "oligonucleotide primers adjacent to a probe region" refers to when 0 or one or more bases separate the primer and probe. The term "overlapping with said probe region" is defined as disclosed in U.S. Pat. No. 7,319,022. The term "Ct" refers to the fractional PCR cycle number at which the reporter fluorescence is greater than the threshold.

Accordingly, in a first aspect, the invention provides methods for detecting a CTX-M nucleic acid in a sample, comprising:

(a) contacting a sample suspected of containing the CTX-M with at least one flap primer having the formula:

$$5'\text{-}[X]_n\text{-}Y\text{-}3' \qquad (I),$$

wherein X represents the 5' portion of the flap primer that is non-complementary to the CTX-M nucleic acid, Y represents the 3' portion of the flap primer that is complementary to the CTX-M nucleic acid, wherein X is about 3-30 nucleotides in length and n=0 or 1, and;

(b) incubating the mixture of step (a) under conditions sufficient to amplify the CTX-M nucleic acid, thereby generating an amplified CTX-M nucleic acid; and (c) detecting the amplified CTX-M nucleic acid.

In some embodiments the at least one flap primer comprises more than one primer sequence. In some embodiments a fluorescence-generating probe is used to detect the amplified CTX-M nucleic acid. The probe may contain a minor groove binder.

In carrying out the preferred methods, the reaction mixture typically comprises at least two flap primers: a forward flap primer and a reverse flap primer. The forward flap primer and the reverse flap primer can be, but need not be, of equal lengths.

In one embodiment, the 5' sequence portion of the flap primer that is non-complementary to the CTX-M nucleic acid (X) is about 1-15 nucleotides in length, usually about 4-14 or about 4-13 nucleotides in length, and more usually about 4-12 nucleotides in length. The 5' sequence portion of the flap primer that is non-complementary to the CTX-M nucleic acid (X) can be 1, 2, 3, 4, 5, 6, 7, 8, 9, 10, 11, 12, 13, 14, or 15 nucleotides in length. In preferred embodiments, the primer is about 30 nucleotides in length overall. If the complementary sequence is less than 30 nucleotides, then a flap may be used to produce a 30-mer primer.

In certain instances, the 3' sequence portion of the flap primer that is complementary to the CTX-M nucleic acid (Y) comprises a greater number of nucleotides than the 5' sequence portion of the flap primer that is non-complementary to the CTX-M nucleic acid (X). For example, the 3' sequence portion of the flap primer that is complementary to the CTX-M nucleic acid (Y) can comprise about 55%, 60%, 65%, 70%, 75%, 80%, 85%, or 90% of the total length of a flap primer.

In certain other instances, the 5' sequence portion of the flap primer that is non-complementary to the CTX-M nucleic acid (X) comprises about an equal number of nucleotides as the 3' sequence portion of the flap primer that is complementary to the CTX-M nucleic acid (Y). For example, the X and Y portions each can be about 4-30, 6-25, 8-20, or 10-15 nucleotides in length, usually about 10-14 or 11-13 nucleotides in length, and more usually about 12 nucleotides in length. The X and Y portions each can be 4, 5, 6, 7, 8, 9, 10, 11, 12, 13, 14, 15, 16, 17, 18, 19, 20, 21, 22, 23, 24, 25, 26, 27, 28, 29, or 30 nucleotides in length.

In another embodiment, the 5' sequence portion of the flap primer that is non-complementary to the CTX-M nucleic acid (X) comprises at least about 60%, 65%, 70%. 75%, 80%, 90%, or 95% adenine or thymine nucleotide bases, or modified bases thereof.

In some embodiments, the 5' sequence portion of the flap primer that is non-complementary to the CTX-M nucleic acid (X) comprises the following sequence or a portion of it: AATAAATCATAA (SEQ ID NO:51). This non-complementary flap sequence may be considered to represent AATAAATCATAA-J (SEQ ID NO:52), in which J is an additional oligonucleotide sequence. In other embodiments, the Y portion of the first flap primer comprises sequences substantially complementary to at least a portion of the CTX-M groups 1 and 9 nucleic acids, namely SEQ ID NOs: 1, 12, 19 or 29, shown below in Table 1, namely primers having sequences with substantial identity to SEQ ID NOs: 2, 3, 6, 7, 8, 13, 14, 16, 17, 20, 21, 24, 25, 30, 31, 33 and 34. "Substantially complementary to at least a portion of" means that the sequence is complementary enough to the CTX-M sequence that it will hybridize and result in amplification of the CTX-M sequence. "Substantial identity" more specifically means about 85% complementary.

The sample is typically obtained from a mammal suspected of having a bacterial infection with potential CTX-M antibiotic resistant involvement. Preferably, the mammal is a human. Examples of samples suitable for use in the methods of the invention include, but are not limited to a rectal swab.

Generally, the methods produce a detectable signal when the probe hybridizes to the amplified target (U.S. Pat. Nos. 7,381,818 and 7,759,126). In addition this method allows the post-amplification melting curve analysis. Alternatively, the fluorescent probe is cleaved by using a nucleic acid polymerase having 5'-3' nuclease activity to yield a fluorescent signal (U.S. Pat. No. 5,538,848). Further, the methods are particularly suited to continuous monitoring of a detectable signal ("real-time detection"). In certain embodiments, simultaneous amplification is detected using a fluorescence-generating probe, for example, a hybridization-based fluorescent probe or a nucleic acid binding fluorescent compound.

Amplified CTX-M groups 1 and 9 nucleic acid can be detected using any of the methods of detection known in the art. For example, detection can be carried out after completion of an amplification reaction (e.g., using ethidium bromide in an agarose gel) or simultaneously during an amplification reaction ("real-time detection") (McPherson et al., PCR Basics, 2000; and Rapid Cycle Real-time PCR Methods and Applications: Quantification, Wittwer et al. (eds.), Springer-Verlag (2004)). Preferably, the amplified CTX-M groups 1 and 9 nucleic acid is detected by hybridization to a probe that specifically binds to the amplified CTX-M groups 1 and 9 nucleic acids. In certain instances, the amplified CTX-M groups 1 and 9 nucleic acids is detected using one or more fluorescence-generating probes. Fluorescence-generating probes include probes that are cleaved to release fluorescence (e.g. U.S. Pat. Nos. 5,538,848, 7,790, 385 etc.), nucleic acid binding compounds (e.g., U.S. Pat. No. 5,994,056; Bengtsson et al., Nucl. Acids Res., 31: e45 (2003)), hybridization-based probes (e.g., U.S. Pat. Nos. 5,925,517, 7,205,105, 7,381,818, etc.), and the like. In certain embodiments, the CTX-M groups 1 and 9 nucleic acid is detected with one or more nucleic acid binding fluorescent compounds (e.g., SYBR® Green 1 (Molecular Probes: Eugene, Oreg.), BOXTOX, BEBO (TATAA Biocenter; Gotenborg, Sweeden), etc.).

In one embodiment, the CTX-M groups 1 and 9 nucleic acid is detected using a fluorescence-generating probe, disclosed in Table 1, that hybridizes to the CTX-M groups 1 and 9 nucleic acids and one or more nucleotide bases of at least one flap primer sequence (typically, the complementary portion, Y). For example, the fluorescence-generating probe can hybridize to the CTX-M groups 1 and 9 nucleic acid and to one or more nucleotide bases of the forward flap primer sequence, one or more nucleotide bases of the reverse flap primer sequence, or simultaneously to one or more nucleotide bases of both the forward and the reverse flap primer sequences. The fluorescence-generating probe can optionally hybridize to the CTX-M groups 1 and 9 nucleic acid and to 1, 2, 3, 4, 5, 6, 7, 8, 9, or 10 nucleotide bases of at least one flap primer sequence, particularly the complementary portion (Y) of a flap primer.

In a preferred embodiment, the fluorescence-generating probe of the invention comprises a sequence having substantial identity to a CTX-M groups 1 or 9 sequence selected from SEQ ID NOs: 4, 9, 10, 11, 18, 22, 26, 27, 28, 32, 35 and 36-46.

In another preferred embodiment, the fluorescence-generating probes of the invention comprise at least one of the following sequences:

```
R_a-G*TCGGCTCGGTACGG-R_b                           (SEQ ID NO: 22)
and

R_a-G*TAGGTTCAGTGCGATCC-R_b                        (SEQ ID NO: 26)
``` wherein G* is the guanine analogue 6-amino-1H-pyrazolo[3,4-d]pyrimidin-4(5H)-one, $R_a$ is independently selected from $(M)_a$-Fl and $(M)_a$-Q, $R_b$ is independently selected from $(M)_a$-Fl and $(M)_a$-Q, and M is a minor groove binder, a is 0 or 1, Fl is a fluorophore with emission wavelength between about 400 and 900 nm and Q is a non-fluorescent quencher, with the proviso that the substitution of $R_a$ and $R_b$ allows quenching of fluorescence when the probe is unhybridized.

In a preferred embodiment Fl is AquaPhluor® 593 with an excitation wavelength of 593 nm.

The primers can incorporate additional features which allow for the detection or immobilization of the primer but do not alter the basic property of the primer, e.g., to act as a point of initiation of nucleic acid synthesis. In some instances, the primers contain one or more non-natural bases or modified bases in either or both the complementary and non-complementary sequence regions of the primer.

In certain instances, amplification is carried out using a polymerase. The polymerase can, but need not, have 5' nuclease activity. In certain other instances, primer extension is carried out using a reverse transcriptase and amplification is carried out using a polymerase.

In another embodiment, the primer sequences overlap, wherein the stability of the overlapping sequence duplex is less than that of the stability of the individual primer target duplexes.

In another aspect, the invention provides methods for simultaneously detecting nucleic acids from CTX-M groups 1 and 9 in a sample, comprising:
(a) contacting a sample suspected of containing the CTX-M groups 1 and 9 nucleic acids with:
 (i) at least one forward flap primer comprising at least one of the following sequences:

```
                                                   (SEQ ID NO: 21)
5'-AATAAATCATAAGCGGATCGCCCGGAATG-3'

(SEQ ID NO: 25)
5'-AATAAATCATAATCGGGTCGCCGGGAATG-3'
``` wherein the underlined nucleotide sequence is non-complementary to the CTX-M groups 1 and 9 sequences; and
(ii) at least one reverse flap primer comprising at least one of the following sequences:

```
                                                   (SEQ ID NO: 20)
5'-AATAAATCATAAACGAAACGTTCCGTCTCGAC-3'

(SEQ ID NO: 24)
5'-AATAAATCATGCGATGAGACGTTTCGTCTGGA-3',
``` wherein the underlined nucleotide sequence is non-complementary to the e CTX-M groups 1 and 9 sequences;
(b) incubating the reaction mixture of step (a) under conditions sufficient to amplify the CTX-M groups 1 and 9 nucleic acids, thereby generating amplified CTX-M groups 1 and 9 nucleic acids from bacteria containing the CTX-M groups 1 and 9 lactamase genes that carry antibiotic resistance; and (c) detecting the amplified CTX-M groups 1 and 9 nucleic acid.

Some embodiments comprise primer ratios that allow asymmetric amplification of the CTX-M groups 1 and 9 nucleic acids.

The sample is typically obtained from a mammal suspected of having an infection of an organism that carries extended spectrum beta-lactamase (ESBL). Preferably, the mammal is a human. Typical sample suitable for use in the methods of the invention contain ESBL containing organisms, preferably rectal swabs.

In some embodiments, continuous monitoring of a detectable signal ("real-time detection") is used to detect the signal. In certain embodiments, simultaneous amplification is detected using a fluorescence-generating probe, for example, a hybridization-based fluorescent probe, a probe with a cleaving-site or a nucleic acid binding fluorescent compound. In some embodiments, end-point fluorescent measurement using a dissociation curve analysis is used to detect the signal.

In yet another aspect, kits are provided for detecting an CTX-M groups 1 and 9 nucleic acid in a sample, comprising:
at least one forward flap primer comprising at least one of the following sequences:

```
                                                   (SEQ ID NO: 21)
5'-AATAAATCATAAGCGGATCGCCCGGAATG-3'

(SEQ ID NO: 25)
5'-AATAAATCATAATCGGGTCGCCGGGAATG-3'
``` wherein the underlined nucleotide sequence is non-complementary to the CTX-M groups 1 and 9 sequences; and
(ii) at least one reverse flap primer comprising at least one of the following sequences:

```
                                                   (SEQ ID NO: 20)
5'-AATAAATCATAAACGAAACGTTCCGTCTCGAC-3'

(SEQ ID NO: 24)
5'-AATAAATCATGCGATGAGACGTTTCGTCTGGA-3',
``` wherein the underlined nucleotide sequence is non-complementary to the e CTX-M groups 1 and 9 sequences.

In certain instances, the kits further comprise a fluorescence-generating probe such as a hybridization-based fluorescent probe, CTX-M groups 1 and 9 or a nucleic acid binding fluorescent compound. In a preferred embodiment, the fluorescence-generating probes comprise the following sequence:

```
                                                   (SEQ ID NO: 4)
R_a-G*TGACI*TGGATGAAAG-R_b-3'

(SEQ ID NO: 9)
R_a-G*TGACGTGGCTCAAAG-R_b (SEQ ID NO: 10)
R_a-G*TGACI*TGGA*TGAAAGGC-R_b (SEQ ID NO: 11)
R_a-G*TGACGTGGCTCAAAGGC-R_b
``` wherein $R_a$ is independently selected from $(M)_a$-Fl and $(M)_a$-Q, $R_b$ is independently selected from $(M)_a$-Fl and $(M)_a$-Q, and M is a minor groove binder, a is 0 or 1, Fl is a fluorophore with emission wavelength between about 400 and 900 nm, and Q is a non-fluorescent quencher, with the proviso that the substitution of $R_a$ and $R_b$ allows quenching of fluorescence when the probe is unhybridized.

In another preferred embodiment, the fluorescence-generating probes comprise at least one of the following sequences:

(SEQ ID NO: 22)
$R_a$-G*TCGGCTCGGTACGG-$R_b$
and (SEQ ID NO: 26)
$R_a$-G*TAGGTTCAGTGCGATCC-$R_b$ wherein G* is 6-amino-1H-pyrazolo[3,4-d]pyrimidin-4 (5H)-one, $R_a$ is independently selected from $(M)_a$-Fl and $(M)_a$-Q, $R_b$ is independently selected from $(M)_a$-Fl and $(M)_a$-Q, and M is a minor groove binder, a is 0 or 1, Fl is a fluorophore with emission wavelength between about 400 and 900 nm, and Q is a non-fluorescent quencher, with the proviso that the substitution of $R_a$ and $R_b$ allows quenching of fluorescence when the probe is unhybridized.

In a preferred embodiment 11 is AquaPhluor 593 with an excitation wavelength of 593 nm (ELITechgroup Molecular Diagnostics, Bothell, Wash.).

In certain other instances, the kits further comprise a control nucleic acid that is suitable for use as an internal control. As a non-limiting example, the control nucleic acid can comprise a nucleic acid sequence SEQ ID NO:47. Preferably, the control nucleic acid comprises the following sequence:

(SEQ ID NO: 47)
5'-CTGCACGGACCAGTTACTTTACGGACCACGTACCGCATTGGTACAAG

ATCTCCGGTAGAAAAAATGAG-3'.

The kits of the invention can also comprise primers and probes directed against the control nucleic acid. As a non-limiting example, a control probe (e.g., a fluorescence-generating probe) and a set of control primers designed against the nucleic acid sequence SEQ ID NO:47 can be included in the kits. Preferably, the control probe and primers have the following sequences:

(SEQ ID NO: 50)
(i) Probe: $R_a$-G*ACCACGTACCGCATTG-$R_b$ wherein G* is the guanine analogue 6-amino-1H-pyrazolo[3,4-d]pyrimidin-4(5H)-one. $R_a$ is independently selected from $(M)_a$-Fl and $(M)_a$-Q, $R_b$ is independently selected from $(M)_a$-Fl and $(M)_a$-Q, and NM is a minor groove binder, a is 0 or 1, Fl is a fluorophore with emission wavelength between about 400 and 900 nm, and Q is a non-fluorescent quencher, with the proviso that the substitution of $R_a$ and $R_b$ allows quenching of fluorescence when the probe is unhybridized; and fluorophore has an emission wavelength different from that of the probe for detecting the nucleic acids from CTX-M groups 1 and 15;

(ii) Primers:
(SEQ ID NO: 48)
CTGCACGGACCAGTTACTTTACG;

(SEQ ID NO: 49)
CTCATTTTTTCTACCGGAGATCTTGT.

In a preferred embodiment Fl is AquaPhluor 525 with an excitation wavelength of 525 nm (ELITechgroup Molecular Diagnostics, Bothell, Wash.), "M" is a minor groove binder such as, for example DPI3, "G*" is PPG, and "Q" is the Eclipse®, Dark Quencher.

In an additional embodiment, the invention provides isolated nucleic acids comprising the sequences set forth in Table 1 below. Table 1 shows primers, probes, and target sequences for CTX-M groups 1 and 9 and an Internal Control.

TABLE 1

| SEQ ID # | Primer or Probe | Sequence >gi\|11321257 for 1 & 15 gi\|16304825 for 9 | Position |
|---|---|---|---|
| | | CTX-M groups 1, 9 | |
| | | Location 1 | |
| 1 | Group 1amplicon | CCAACGGGCGCAGCTGGTGACGTGGATGA AAGGCAATACTACCGGTGCAGCGAG | grp1 615-668 |
| 2 | CTX-E1 | <u>AATAAATCATAA</u>CTCGCTGCACCGGTPGT A | grp1, 15 651-668 |
| 3 | CTX-L1 | <u>AATAAATCATAA</u>CCAACGGGCGCAGCT | grp 1 615-629 |
| 4 | CTX-AP593- I | $R_a$-G*TGACI*<u>TGGATGAAAG</u>-$R_b$ | grp 1 631-646 |
| 5 | Group 9 amplicon | GAAACCCAGCGGGCGCAGTTGGTGACGTG GCTCAAAGGCAATACGACCGGCGCAGCCA G | grp9 741-998 |
| 6 | CTX-E2 | <u>AATAAATCATAA</u>TGGCTGCGCCGGTCGTA | grp9 782-798 |
| 7 | CTX-L2 | <u>AATAAATCATAA</u>GAAACCCAGCGGGCGCAG TT | grp9 741-760 |
| 8 | CTX-L3 | <u>AATAAATCATAA</u>CCAGCGGGCGCAGTT | Grp9 74 -760 |
| 9 | CTX-AP593-2 | $R_a$-G*TGACGTGGCTCAAAG-$R_b$ | grp 9 762-777 |
| 10 | CTX-AP593-7 | $R_a$-G*TGACI*TGG<u>A</u>*TGAAAGGC-$R_b$ | grp 1 631-648 |
| 11 | CTX-AP-8 | $R_a$-G*TGACGTGGCTCAAAGGC-$R_b$ | grp9 761-779 |

TABLE 1-continued

CTX-M groups 1, 9

Location 2

| | | | |
|---|---|---|---|
| 12 | Group 1, 15 amplicon | CCGAATCTGTTAAATCAGCGAGTTGAGATC AAAAAATCTGACCTTGTTAACTATAATCCG ATTGCGGAAAAGCACGTCAATGGGACGAT GTCACTGGCTGAG | |
| 13 | CTX-L5 | <u>AATAAATCA</u>CTCAGCCAGTGACATCGTCCC AT | grp 1, 349-372 |
| 14 | CTX-E4 | <u>AATAAATCATA</u>CCGAATCTGTTAAATC<u>A</u>*G CGAGT | grps 1 270-293 |
| 15 | Group 9 amplicon | AGCTGCTTAATCAGCCTGTCGAGATCAAGC CTGCCGATCTGGTTAACTACAATCCGATTG CCGAAAAACACGTCAACGGCACAATGACG CT | |
| 16 | CTX-L4 | <u>AATAAATCATA</u>ACGTCATTGTGCCGTTGAC GT | grp9 475-494 |
| 17 | CTX-E3 | <u>AATAAATCATA</u>GCTGCTTAATCAGCCTGTC GA | grp9 407-427 |
| 18 | CTX-AP593-3 | R<sub>a</sub>-G*CA*ATCGGA*T*T*I*TAGT-R<sub>b</sub> | all grps 1 & 15: 451-466 9: 382-397 |

Location 3

| | | | |
|---|---|---|---|
| 19 | | ACGAAACGTTCCGTCTCGACCGTACCGAG CCGACGTTAAACACCGCCATTCCGGGCGA TCCGC | grp 1 479-541 |
| 20 | CTX-E6 | <u>AATAAATCATA</u>AACGAAACGTTCCGTCTC GAC | grp1 479-498 |
| 21 | CTX-L7 | <u>AATAAATCATA</u>AGCGGATCGCCCGGAATG | grp 1 525-541 |
| 22 | CTX-AP593-11 | R<sub>a</sub>-G*TCGGCTCGGTACGG-R<sub>b</sub> | grp1 498-512 |
| 23 | grp 1, 5 amplicon | GCGATGAGACGTTTCGTCTGGATCGCACTG AACCTACGCTGAATACCGCCATTCCCGCG ACCCGAGAGAC | Group9 |
| 24 | CTX-E5 | <u>AATAAATCAT</u>GCGATGAGACGTTTCGTCTG GA | grp9 607-628 |
| 25 | CTX-L6 | <u>AATAAATCATA</u>ATCGGGTCGCCCGGGAATG | grp9 656-672 |
| 26 | CTX-AP593-4 | R<sub>a</sub>-G*TAGGTTCAGTGCGATCC-R<sub>b</sub> | grp9 626-643 |
| 27 | CTX-AP593-5 | R<sub>a</sub>-G*TCGGCTCGGTACGG-R<sub>b</sub> | grp1, 15 |
| 28 | CTX-AP593-10 | R<sub>a</sub>-G*TAGGTTCAGTGCGATCC-R<sub>b</sub> | grp9 626-643 |

4<sup>th</sup> location (variation of the 2<sup>nd</sup> location)

| | | | |
|---|---|---|---|
| 29 | | ACGTCAACGGCACAATGACGCTGGCAGAA CTGAGCGCGGCCGCGTTGCAGTACAGCGA CAATACCGCCATGAACAAATTGATTGCCC AGC | Group 1: |
| 30 | CTX-L8 | <u>ATCATAA</u>CGTGAGCAATCAGCTTATTCATC GC | group 1 409-433 |
| 31 | CTXM-E7 | <u>ATAAATCATA</u>ACGTCAACGGCACAATGAC GCT | group 1 345-365 |
| 32 | CTX-AP593-6 | R<sub>a</sub>-G*T*T*I*TCGCTGTA*CTGTAG-R<sub>b</sub> | all grps |
| 33 | CTX-L9 | <u>ATCATAA</u>GCTGGGCAATCAATTTGTTCAT GGC | group 9 409-433 |
| 34 | CTXM-E8 | <u>ATAAATCATA</u>ACGTCAACGGCACAATGAC GCT 71 | group 9 476-496 |
| 35 | CTX-AP593-12 | R<sub>a</sub>-GTTI*TCGCTGTACTGTA<u>A</u>*G-R<sub>b</sub> | all grps |

| | Group 9 | Specific Probes | |

Amplicon 1 (starting from 5' end of alignment)

| | | | |
|---|---|---|---|
| 36 | | R<sub>a</sub>-ATGGTG<u>A</u>CAAAG<u>A</u>GAGT-R<sub>b</sub> | |
| 37 | | R<sub>a</sub>-CCGCGAACATCATCCGT-R<sub>b</sub> | |

TABLE 1-continued

CTX-M groups 1, 9

Amplicon 2

| | |
|---|---|
| 38 | $R_a$-CGGCGGCGTGCATTC-$R_b$ |
| 39 | $R_a$-GCCCAGCAGCAGCG-$R_b$ |

Amplicon 3

| | |
|---|---|
| 40 | $R_a$-CCCGGGAGGCGTGA-$R_b$ |
| 41 | $R_a$-GATCGCGCGGGCAA-$R_b$ |

Amplicon 4

| | |
|---|---|
| 42 | $R_a$-TCATGCGCTGGGCGAA-$R_b$ |
| 43 | $R_a$-AGCTTACGCTGGGTCATG-$R_b$ |
| 44 | $R_a$-GAGCCACGTCACCAACT-$R_b$ |

Amplicon 5

| | |
|---|---|
| 45 | $R_a$-GGTGATCTGGCCGCA-$R_b$ |
| 46 | $R_a$-GGCGCACGACCC-$R_b$ |

I* = 3-(aminobutynyl)-1H-pyrazolo[3,4-d]pyrimidin-4(5H)-one
G* = 6-amino-1H-pyrazolo[3,4-d]pyrimidin-4(5H)-one (PPG or Super G ®)
A* = 4-(4,6-Diamino-1H-pyrazolo[3,4-d]pyrimidin-3-yl)-but-3-yn-1-ol (Super A ®)
T* = 5-(4-hydroxy-but-1-ynyl)-1H-pyrimidine-2,4-dione (Super T ®)

Internal Control

| | | | |
|---|---|---|---|
| 47 | Amplicon | CTGCACGGACCAGTTACTTTACGGACCACG TACCGCATTGGTACAAGATCTCCGGTAGA AAAAATGAG | |
| 48 | E6132-L | CTGCACGGACCAGTTACTTTACG | 0.20 µM |
| 49 | E6132-E | CTCATTYFITCTACCGGAGATCTTGT | 0.20 µM |
| 50 | E6132-AP525-TM3 | $R_a$-G*ACCACGTACCGCATTG-$R_b$ | 0.10 µM |

F1 = AquaPhluor525 with an excitation wavelength of 525 nm

Most preferred primer and probe sequences for the detection of CTX-M groups 1 and 9 nucleic acid and most preferred IC sequences are shown in Table 2 below.

TABLE 2

| SEQ ID # | Name | Sequence 5'-3' | 1X |
|---|---|---|---|
| | | CTX-M groups 1 and 9 Primer and probe sequences | |
| 26 | CTXM-AP593-4 | $R_a$-G*TAGGTTCAGTGCGATCC-$R_b$ | 0.10 µM |
| 27 | CTXM-AP593-5 | $R_a$-G*TCGGCTCGGTACGG-$R_b$ | 0.10 µM |
| 25 | CTXM-L6 | AATAAATCATAATCGGGTCGCCGGGAATG | 0.50 µM |
| 21 | CTXM-L7 | AATAAATCATAAGCGGATCGCCCGGAATG | 0.50 µM |
| 24 | CTXM-E5 | AATAAATCATGCGATGAGACGTTTCGTCTGGA | 0.50 µM |
| 20 | CTXM-E6 | AATAAATCATAAACGAAACGTTCCGTCTCGAC | 0.50 µM |

$R_a$ = F1 and F1 = AquaPhluor 593 with an excitation wavelength of 593 nm
$R_b$ = Q-M where Q = Eclipse ® Dark Quencher and M = $DPI_3$ and G = Super G

| | | Internal Control Primer and Probe Sequences | |
|---|---|---|---|
| 48 | E6132-L | CTGCACGGACCAGTTACTTTACG | 0.20 µM |
| 49 | E6132-E | CTCATTTTTTCTACCGGAGATCTTGT | 0.20 µM |
| 50 | E6132-AP525-TM3 | Ra-G*ACCACGTACCGCATTG-$R_b$ | 0.10 µM |

$R_a$ = F1 and F1 = AquaPhluor 525 with and excitation wavelength of 525 nm
$R_b$ = Q-M where Q = Eclipse ® Dark Quencher and M = $DPI_3$ and G = Super G TABLE 2-continued

| SEQ ID # | Name | Sequence 5'-3' | 1X |
|---|---|---|---|
| | | Non-complementary Flap Sequence | |
| 51 | | AATAAATCATAA | NA |
| 52 | | AATAAATCATAA-J | |

J = an oligonucleotide sequence

In one aspect, the present invention provides target sequences suitable for specific detection and amplification of extended beta-lactamase resistant genes that involves CTX-M groups 1 and 9.

More specifically, a method of detecting the presence or absence of extended beta-lactamase resistant nucleic acids in samples that involve CTX-M groups 1 and 15, the method comprises contacting said sample with one or more oligonucleotides designed to hybridize to any one of SEQ ID NO: 1, 12, 19 or 29 or a complement under conditions which discriminate groups 1 and 15 nucleic acid and detecting if the hybridization of said one or more oligonucleotides to SEQ ID NO: 1, 12, 19 or 29 or a complement thereof has occurred, wherein said hybridization detects the presence or absence of CTX-M groups 1 and 15 nucleic acid.

In another embodiment a method of detecting the presence or absence of extended beta-lactamase resistant nucleic acids in samples that involve CTX-M group 9 comprises contacting said sample with one or more oligonucleotides designed to hybridize to any one of SEQ ID NO: 5, 15, or 23 or a complement under conditions which discriminate group 9 nucleic acid and detecting if the hybridization of said one or more oligonucleotides to SEQ ID NO: 5, 15, or 23 or a complement thereof has occurred, wherein said hybridization detects the presence or absence of CTX-M group 9 nucleic acid.

In one aspect the detection of presence or absence of extended beta-lactamase resistant gene nucleic acids as defined in Table 1 that involves CTX-M groups 1 and 9 by hybridization comprises nucleic acid-based amplification.

In another aspect the generated amplicon is at least about 30 nucleotide bases long.

Other aspects include the one or more oligonucleotides hybridizing to the nucleic acids of extended beta-lactamase resistant genes sequences as defined in Table 1 that involve CTX-M groups 1 and 9 comprises primers and/or probes.

The one or more oligonucleotide primers hybridizing to nucleic acids of CTX-M group 1 may be selected from sequences SEQ ID NO: 2, 3, 13, 14, 20, 21, 30 and 31.

The one or more oligonucleotide primers hybridizing to nucleic acids of CTX-M group 9 may be selected from sequences comprising SEQ ID NO: 6, 7, 8, 16, 17, 24, 25, 33 and 34.

Nucleic acid-based amplification products generated from CTX-M groups 1 nucleic acid may be detected by one or more oligonucleotide probes comprising sequences selected from SEQ ID NOs: 4, 18, 22, and 27.

In some embodiments $R_a$=M-Fl where M is a minor groove binder and Fl is a fluorophore and $R_b$=quencher.

Nucleic acid-based amplification products generated from CTX-M group 9 nucleic acid may be detected by one or more oligonucleotide probes comprising sequences selected from SEQ ID NOs: 9, 11, 26, 28, and 36-46.

The present method provides oligonucleotide primers ("overhang primers," "flap primers," or "adapter primers") which are most generally noted as 5'-$(X)_p$—Y-3' primers where p=0 or 1. X represents the sequence portion of the primer that is non-complementary to the CTX-M groups 1 and 9 nucleic acid, and Y represents the sequence portion of the primer that is complementary to the CTX-M groups 1 and 9 nucleic acid.

Accordingly, in one group of embodiments, the primer has the formula:

$$5'\text{-}(X)_p\text{-}Y\text{-}3' \qquad (I).$$

wherein X represents the 5' sequence of the primer non-complementary to the CTX-M groups 1 and 9 nucleic acid, Y represents the complementary 3' sequence of the primer, p is 0 or 1, and X—Y represents the nucleic acid oligomer primer. In certain further embodiments, X is $[A\text{-}B]_m$ and Y is $[A\text{-}B]_n$, wherein A represents a sugar phosphate backbone, modified sugar phosphate backbone, locked nucleic acid backbone, or a variant thereof in any combination as used in nucleic acid preparation; B represents a nucleic acid base or a modified base of a base; and the subscripts m and n are integers of from about 4-30 or 5-25, 7-20, or 9-15, and more usually about 12. In certain embodiments, the values of the subscripts m and n are equal, for example, both m and n simultaneously can be an integer of from about 5-25, 7-20, or 9-15, and more usually about 12.

Primers and probes were designed to amplify and detect regions of the blaCTX-M genes blaCTX-M gene located on a transferable plasmid and more specifically of CTX-M groups 1 and 9 nucleic acids that have substantial or absolute homology between members of respective groups. In some embodiments, the primers are flap primers comprising the following formula:

$$5'\text{-}(X)_p\text{-}Y\text{-}3' \qquad (I),$$

wherein X represents the 5' portion of the flap primer that is non-complementary to the CTX-M groups 1 and 9 nucleic acid, Y represents the 3' portion of the flap primer that is complementary to the CTX-M groups 1 and 9 nucleic acid, and p is about 3-30, 5-25, 7-20, or 9-15.

The 5'-non-complementary sequences of the primers of this invention can be modified as taught in U.S. Patent Application 2007/0048758.

The primers and probes of the present invention are generally prepared using solid phase methods known to those of skill in the art. In general, the starting materials are commercially available, or can be prepared in a straightforward manner from commercially available starting materials using suitable functional group manipulations as described in, for example, March et al., ADVANCED ORGANIC CHEMISTRY—Reactions, Mechanisms and Structures, 4th ed., John Wiley & Sons, New York, N.Y. (1992).

In one embodiment, the primers and probes of the invention can comprise any naturally occurring nucleotides, non-naturally occurring nucleotides, or modified nucleotides known in the art (see, e.g., U.S. Patent Publication No.

20050118623; and U.S. Pat. No. 6,949,367, U.S. Patent Publication No. 20120244535).

The ability to design probes and primers in a predictable manner using an algorithm that can direct the use or incorporation of modified bases, minor groove binders, fluorphores, and/or quenchers based on their thermodynamic properties have been described in, e.g., U.S. Pat. No. 6,683,173. Accordingly, the use of any combination of normal bases, unsubstituted pyrazolo[3,4-d]pyrimidine bases (e.g., PPG and PPA), 3-substituted pyrazolo[3,4-d]pyrimidines, modified purines, modified pyrimidines, 5-substituted pyrimidines, universal bases, sugar modifications, backbone modifications, and/or minor groove binders to balance the Tm (e.g., within about 5-8° C.) of a hybridized product with a modified nucleic acid, reduce G-G self-association or to accommodate mismatches in primer or probe is contemplated by the present invention. Co-owned U.S. Patent Application 2012/0244535, incorporated by reference, provides additional explanation as to how to address primers and probes with as many as five mismatches in a primer.

Detailed descriptions of the chemistry used to synthesize oligonucleotides by the phosphoramidite method are provided in U.S. Pat. Nos. 4,458,066 and 4,415,732; Caruthers et al., Genetic Engineering, 4:1-17 (1982); and Users Manual Model 392 and 394 Polynucleotide Synthesizers, pages 6-1 through 6-22, Applied Biosystems. Part No. 901237 (1991). Labeled oligonucleotides can be synthesized by chemical synthesis. e.g., by a phosphoramidite method, a phosphite-triester method, and the like, (see, e.g., Gait. Oligonucleotide Synthesis, IRL Press (1990)). Labels can be introduced during enzymatic synthesis utilizing labeled nucleoside triphosphate monomers, or introduced during chemical synthesis using labeled non-nucleotide or nucleotide phosphoramidites, or may be introduced subsequent to synthesis.

A variety of linking groups and methods are known to those of skill in the art for attaching fluorophores, quenchers, and minor groove binders to the 5' or 3' termini of oligonucleotides. See, for example, Eckstein, (ed.), Oligonucleotides and Analogues: A Practical Approach, IRL Press, Oxford (1991); Zuckerman et al., Nuc. Acids Res., 15:5305-5321 (1987); Sharma et al., Nuc. Acids Res., 19:3019 (1991); Giusti et al., PCR Methods and Applications, 2:223-227 (1993), U.S. Pat. Nos. 4,757,141 and 4,739,044; Agrawal et al., Tetrahedron Letters, 31:1543-1546 (1990); Sproat et al., Nuc. Acids Res., 15:4837 (1987); Nelson et al., Nuc. Acids Res., 17:7187-7194 (1989); and the like. Still other commercially available linking groups can be used that can be attached to an oligonucleotide during synthesis and are available from, e.g., Clontech Laboratories (Palo Alto, Calif.). Other methodologies for attaching a fluorophore to an oligonucleotide portion involve the use of phosphoramidite chemistry at the conclusion of solid phase synthesis by way of dyes derivatized with a phosphoramidite moiety. See, e.g., U.S. Pat. Nos. 5,231,191; 4,997,928; 6,653,473; 6,790,945; and 6,972,339; and PCT Patent Publication No. WO 01/42505.

IV. Additional Amplification Reaction Components

Buffers

Buffers that may be employed are borate, phosphate, carbonate, barbital, Tris, etc., based buffers (see, e.g., U.S. Pat. No. 5,508,178). The pH of the reaction should be maintained in the range of from about 4.5 to about 9.5 (see, e.g., U.S. Pat. No. 5,508,178). The standard buffer used in amplification reactions is a Tris based buffer between 10 and 50 mM with a pH of around 8.3 to 8.8 (see, e.g., Innis et al., supra).

One of skill in the art will recognize that buffer conditions should be designed to allow for the function of all reactions of interest. Thus, buffer conditions can be designed to support the amplification reaction as well as any subsequent restriction enzyme reactions. A particular reaction buffer can be tested for its ability to support various reactions by testing the reactions both individually and in combination.

Salt Concentration

The concentration of salt present in the reaction can affect the ability of primers to anneal to the target nucleic acid (see, e.g., Innis et al., supra). Potassium chloride can be added up to a concentration of about 50 mM to the reaction mixture to promote primer annealing. Sodium chloride can also be added to promote primer annealing (see, e.g., Innis et al., supra).

Magnesium Ion Concentration

The concentration of magnesium ion in the reaction can affect amplification of the target nucleic acid sequence (see, e.g., Innis et al., supra). Primer annealing, strand denaturation, amplification specificity, primer-dimer formation, and enzyme activity are all examples of parameters that are affected by magnesium concentration (see, e.g., Innis et al., supra). Amplification reactions should contain about a 0.5 to 6.0 mM magnesium concentration excess over the concentration of dNTPs. The presence of magnesium chelators in the reaction can affect the optimal magnesium concentration. A series of amplification reactions can be carried out over a range of magnesium concentrations to determine the optimal magnesium concentration. The optimal magnesium concentration can vary depending on the nature of the target CTX-M groups 1 and 9 nucleic acid and the primers being used, among other parameters.

Deoxynucleotide Triphosphate Concentration

Deoxynucleotide triphosphates (dNTPs) are added to the reaction to a final concentration of from about 20 µM to about 300 µM. Typically, each of the four dNTPs (G, A, C, T) are present at equivalent concentrations (see, e.g., Innis et al., supra). In some embodiments, uracil N-glycosylase is used with dUTP (instead of TTP) in PCR reactions.

Nucleic Acid Polymerases

A variety of DNA dependent polymerases are commercially available that will function using the present methods and compositions. For example, Taq DNA Polymerase may be used to amplify target DNA sequences. The PCR assay may be carried out using as an enzyme component a source of thermostable DNA polymerase suitably comprising Taq DNA polymerase which may be the native enzyme purified from *Thermus aquaticus* and/or a genetically engineered form of the enzyme. Other commercially available polymerase enzymes include, e.g., Taq polymerases marketed by Qiagen, New England Biolabs, Applied Biosystems, Promega or Pharmacia. Other examples of thermostable DNA polymerases that could be used in the invention include DNA polymerases obtained from, e.g., *Thermus* and *Pyrococcus* species. Concentration ranges of the polymerase may range from 1-5 units per reaction mixture. The reaction mixture is typically between about 5 µl and about 100 µl.

Other Agents

Additional agents are sometimes added to the reaction to achieve the desired results. For example, DMSO can be added to the reaction, but is reported to inhibit the activity of Taq DNA Polymerase. Nevertheless, DMSO has been recommended for the amplification of multiple target sequences in the same reaction (see, e.g., Innis et al., supra). Stabilizing agents such as gelatin, bovine serum albumin, and non-ionic detergents (e.g., Tween-20) are commonly added to amplification reactions (see, e.g., Innis et al., supra). Additionally, betaine (Sigma-Aldrich; St. Louis, Mo.), an isostabilizing agent, can be added to equalize the contribution of GC- and AT-base pairing to the stability of the nucleic acid duplex.

Minor Groove Binders

Minor groove binder oligonucleotide conjugates (or "probes") are described in, e.g., U.S. Pat. No. 6,312,894. These conjugates form hyper-stabilized duplexes with complementary DNA. In particular, sequence specificity of short minor groove binder probes is excellent for high temperature applications such as PCR. The probes/conjugates of the present invention will also optionally have a covalently attached minor groove binder. A variety of suitable minor groove binders have been described in the literature (see, e.g., U.S. Pat. No. 5,801,155; Wemmer et al., Curr. Opin. Struct. Biol., 7:355-361 (1997); Walker et al., Biopolymers, 44:323-334 (1997); Zimmer et al., U. Prog. Biophys. Molec. Bio., 47:31-112 (1986); and Reddy et al., J. W., Pharmacol. Therap., 84:1-111 (1999)).

The minor groove binder-quencher-oligonucleotide-fluorophore conjugates can be in a linear arrangement (as suggested by the formula 5'-M-Q-ODN-Fl-3' or 5'-M-Fl-ODN-Q-3') or in a branched arrangement wherein the quencher (Q) and the minor groove binder (M) are attached to a linking group that serves to join ODN, Q, and M. Additionally, the quencher can be attached at the distal (relative to attachment to ODN) terminus of the minor groove binder (e.g., 5'-Q-M-ODN-Fl-3'). Each of the arrangements is meant to be included when the linear abbreviation (M-Q-ODN-Fl) is used. Additionally, the minor groove binder and quencher portions each can be attached at either the 3' or 5' end of the oligonucleotide, or an internal position of the oligonucleotide, so long as such attachment does not interfere with the quenching mechanisms of the conjugate. Generally, this can be accomplished through the use of a suitable linking group (see, e.g., U.S. Pat. Nos. 7,205,105 and 7,381,818).

Suitable methods for attaching minor groove binders (as well as reporter groups such as fluorophores and quenchers described below) through linkers to oligonucleotides are described in, for example, U.S. Pat. Nos. 5,512,677; 5,419,966; 5,696,251; 5,585,481; 5,942,610; and 5,736,626.

The minor groove binder is generally attached to the 3' or 5' position of the oligonucleotide portion via a suitable linking group. Attachment at the 5' end provides both a benefit of hybrid stability, since melting of an oligonucleotide duplex begins at the termini, but also reduces and/or prevents nuclease digestion of the probe during amplification reactions.

The location of a minor groove binder within a minor groove binder-oligonucleotide conjugate can also affect the discriminatory properties of such a conjugate. An unpaired region within a duplex will result in changes in the shape of the minor groove in the vicinity of the mispaired base(s). Since minor groove binders fit best within the minor groove of a perfectly-matched DNA duplex, mismatches resulting in shape changes in the minor groove would reduce binding strength of a minor groove binder to a region containing a mismatch. Hence, the ability of a minor groove binder to stabilize such a hybrid would be decreased, thereby increasing the ability of a minor groove binder oligonucleotide conjugate to discriminate a mismatch from a perfectly matched duplex. On the other hand, if a mismatch lies outside of the region complementary to a minor groove binder oligonucleotide conjugate, discriminatory ability for unconjugated and minor groove binder-conjugated oligonucleotides of equal length is expected to be approximately the same. Since the ability of an oligonucleotide probe to discriminate single base pair mismatches depends on its length, shorter oligonucleotides are more effective in discriminating mismatches. The primary advantage of the use of minor groove binder oligonucleotides conjugates in this context lies in the fact that much shorter oligonucleotides compared to those used in the prior art (i.e., 20 mers or shorter), having greater discriminatory powers, can be used, due to the pronounced stabilizing effect of minor groove binder conjugation.

The selection of minor groove binders and available minor groove binders have been disclosed in U.S. Pat. Nos. 5,801,155, 6,312,894 and 7,582,739.

Quenchers

Recently developed detection methods employ the process of fluorescence resonance energy transfer (FRET) for the detection of probe hybridization rather than direct detection of fluorescence intensity. In this type of assay, FRET occurs between a donor fluorophore (reporter) and an acceptor molecule (quencher) when the absorption spectrum of the quencher molecule overlaps with the emission spectrum of the donor fluorophore and the two molecules are in close proximity. The excited-state energy of the donor fluorophore is transferred to the neighboring acceptor by a resonance dipole-induced dipole interaction, which results in quenching of the donor fluorescence. If the acceptor molecule is a fluorophore, its fluorescence may sometimes be increased. The efficiency of the energy transfer between the donor and acceptor molecules is highly dependent on distance between the molecules. Equations describing this relationship are known. The Forster distance (Ro) is described as the distance between the donor and acceptor molecules where the energy transfer is 50% efficient. Other mechanisms of fluorescence quenching are also known, such as collisional and charge transfer quenching. There is extensive guidance in the art for selecting quencher and fluorophore pairs and their attachment to oligonucleotides (see, e.g., Haugland, Handbook of Fluorescent Probes and Research Chemicals, Ninth Edition, Molecular Probes, Eugene, Oreg. (2002) and the Web Edition at www.probes.com/handbook; and U.S. Pat. Nos. 3,996,345 and 4,351,760). Preferred quenchers are described in U.S. Pat. Nos. 6,727,356 and 6,790,945. Additional mono- and bis-azo dyes are commercially available from Berry and Associates (Dexter, Mich.) and Glen Research (Sterling, Va.).

Fluorophores

Fluorophores useful in the present invention are generally fluorescent organic dyes that have been derivatized for attachment to the terminal 3' or 5' carbon of the oligonucleotide probe, preferably via a linking group. One of skill in the art will appreciate that suitable fluorophores are selected in combination with a quencher that is typically also an organic dye, which may or may not be fluorescent. Examples of these and other suitable dye classes can be found in Haugland et al., Handbook of Fluorescent Probes and Research Chemicals, Sixth Ed., Molecular Probes, Eugene, Ore. (1996); U.S. Pat. Nos. 3,194,805; 3,128,179; 5,187,288; 5,188,934; 5,227,487; 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP Patent No. 1408366; Still other dyes are provided via online sites such as http://www.zeiss.com. Preferred phosphonate dyes are disclosed in co-owned U.S. Pat. No. 7,671,218, U.S. Pat. Nos. 7,767,834 and 8,163,910.

There is a great deal of practical guidance available in the literature for selecting appropriate fluorophore-quencher pairs for particular probes. Haugland supra and the Web Edition at www.probes.com/handbook and the like. Examples of these and other suitable dye classes can be found in Haugland et al., Handbook of Fluorescent Probes and Research Chemicals, Sixth Ed., Molecular Probes. Eugene, Ore. (1996); U.S. Pat. Nos. 3,194,805; 3,128,179; 5,187,288; 5,188,934; 5,227,487, 5,248,782; 5,304,645; 5,433,896; 5,442,045; 5,556,959; 5,583,236; 5,808,044; 5,852,191; 5,986,086; 6,020,481; 6,162,931; 6,180,295; and 6,221,604; EP Patent No. 1408366; Still other dyes are provided via online sites such as http://www.zeiss.com. Methods for derivatizing fluorophores and quenchers for covalent attachment via common reactive groups are well known. See, for example, Haugland, supra; and U.S. Pat. Nos. 3,996,345 and 4,351,760.

Preferred fluorophores are those based on xanthene dyes, a variety of which are available commercially with substituents useful for attachment of either a linking group or for direct attachment to an oligonucleotide. Most preferred phosphonate dyes are disclosed in co-owned U.S. Pat. No. 7,671,218, U.S. Pat. Nos. 7,767,834 and 8,163,910.

EXAMPLES

The following examples are provided to illustrate, but not to limit, the subject matter described herein.

Oligonucleotides

Primers were synthesized using standard phosphoramidite chemistry. The 5'-M-Fl-ODN-Q and Fl-ODN-Q-M probes were prepared by automated DNA synthesis on a M-FL- or M-Q-modified polystyrene solid support, respectively, using 5-β-cyaoethyl- or 3'-β-cyanoethyl phosphoramidites (Glen Research; Sterling, Va.) designed for synthesis of oligonucleotide segments in the 5'→3 or 3'→5' direction, respectively. Oligonucleotide synthesis was performed on an ABI 394 synthesizer according to the protocol supplied by the manufacturer using a 0.02M iodine solution. Modified and universal bases were synthesized based on the methods disclosed in U.S. Pat. Nos. 6,949,367, 6,127,121 and U.S. Patent Publication No. 20120244535. Fluorophore reporting dyes or quenchers were introduced at the last step of the synthesis using the corresponding phosphoramidites as required. All oligonucleotides were purified by reverse phase HPLC.

PCR

Real-time PCR was performed using the RGQ MDx real-time PCR amplification instrumentation on samples from human rectal swabs from symptomatic and asymptomatic patients material extracted with QIAsymphony SP/AS DNA extraction system (QIAGEN Inc., Valencia, Calif.) in a diagnostic assay to detect ESBL DNA. The assay mixture contains the following components:

Master Solution A: Includes the CTX-M group 1, 9-specific and Internal Control probes and primers, PCR buffer, HotStartTaq QR2 DNA Polymerase. Uracil N-Glycosylase, and deoxynucleotides (dATP, dCTP, dGTP, and dUTP). 23 µL of the Master A reagent mix is used for each 40 µL PCR reaction. The following formulation of Master A was selected as shown in Table 3 below.

Master Solution B: an 80 mM MgCl$_2$ solution. 2 µL of the Master B reagent mix is used for each 40 µL PCR reaction for the final concentration of 4 mM.

Sample: 15 µL of the extracted sample.

Example 1

This example illustrates the real-time PCR detection of CTX-M15 DNA (member of CTX-M group 1) extracted from *E. coli* ATCC BAA-2326 alone and with Internal Control (biplex).

Nucleic acid was extracted with the Qiagen QIAsymphony SP/AS DNA extraction system from *E. coli* ATCC BAA-2326 according to instrument instructions (QIAsymphony® SP/AS User Manual, April 2012). The biplex MGB TaqMan assay was performed using 35 µL Master Solution A that includes the primers, probes and reagents shown in Table 3, 2 µL Master Solution B as described above and 15 µL extracted sample. Table 3 below shows the primers, probes, and reagents of Master Solution A.

TABLE 3

| SEQ ID NO: | Component Name | Oligonucleotide Sequence | Final 1X Concen. |
|---|---|---|---|
| 25 | CTX-L6 | AATAAATCATAATCGGGTCGCCGGGAATG | 0.500 µM |
| 21 | CTX-L7 | AATAAATCATAAGCGGATCGCCCGGAATG | 0.500 µM |
| 24 | CTX-E5 | AATAAATCATGCGATGAGACGTTTCGTCTGGA | 0.500 µM |
| 20 | CTX-E6 | AATAAATCATAAACGAAACGTTCCGTCTCGAC | 0.500 µM |
| 26 | CTX-AP593-4 | AP593-G*TAGGTTCAGTGCGATCC-EDQ-MGB | 0.100 µM |
| 27 | CTX-AP593-5 | AP593-G*TCGGCTCGGTACGG-EDQ-MGB | 0.100 µM |
| 48 | E6132-L | CTGCACGGACCAGTTACTTTACG | 0.200 µM |
| 49 | E6132-E | CTCATTTTTTCTACCGGAGATCTTGT | 0.200 µM |
| 50 | E6132-AP525-TM3 | AP525-G*ACCACGTACCGCATTG-EDQ-MGB | 0.100 µM |
|  | 100 mM dATP | N/A | 0.200 mM |
|  | 100 mM dCTP | N/A | 0.200 mM |
|  | 100 mM dGTP | N/A | 0.200 mM |
|  | 100 mM dUTP | N/A | 0.400 mM |
|  | 10X PCR Buffer | N/A | 1X |
|  | HotStar Taq QR2 DNA Polymerase | 5U/U/µL | 0.10 U/µL |
|  | UNG | 1U/µL | 0.01 U/µL |
|  | Molecular Biology Grade Water | N/A | N/A |

The PCR cycling conditions are shown in Table 4 below.

TABLE 4

| Stage | Temp (° C.) | Time |
|---|---|---|
| UNG Treatment | 50° C. | 2 min. |
| Polymerase Activation | 95° C. | 15 Min. |

TABLE 4-continued

| Stage | Temp (° C.) | Time |
|---|---|---|
| UNG Deactivation | | |
| Denaturation: | 95° C. | 10 Sec. |
| Annealing: | 56° C. | 30 Sec. |
| Extension: | 72° C. | 15 Sec. |

In FIG. 1 is shown the real-time titration (the tenfold titration (100 pg-1 fg)) of CTX-M15 DNA extracted from *E. coli* ATCC BAA-2326 alone and with Internal Control.

Figure 2:
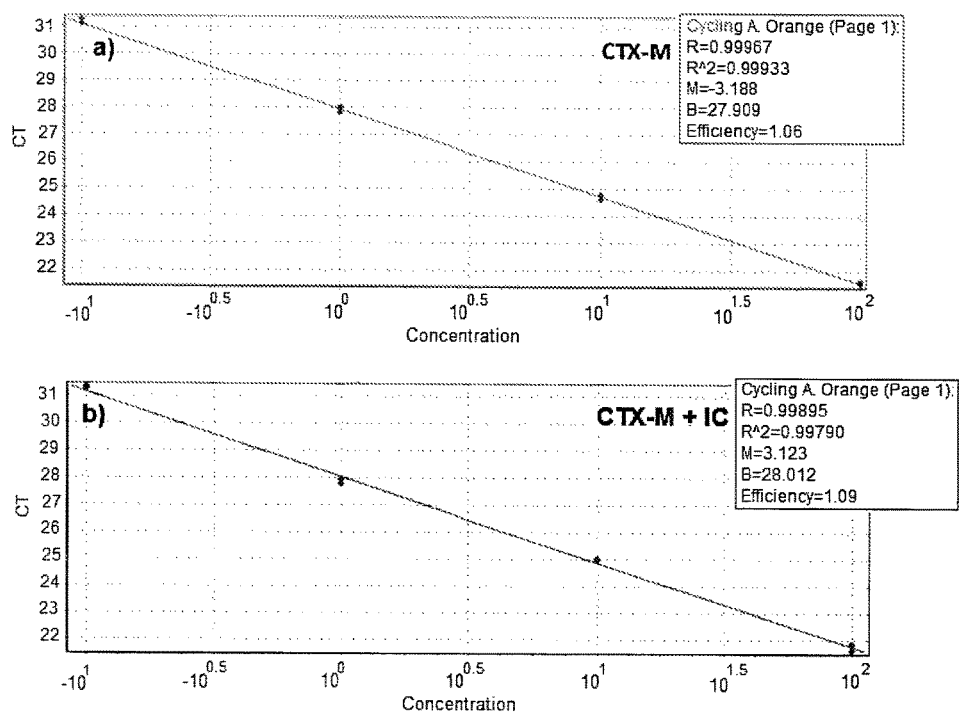
FIG. 2 shows single- and bi-plex amplification data for the CTX-M15- and CTC-M15+IC shown in FIG. 1 re-plotted as linear curves.

The single- and bi-plex amplification data of FIG. 1 was re-plotted as linear curves in FIGS. 2a and 2b. As shown in FIGS. 2a and 2b the slopes of the CTX-M15- and CTC-M15+IC curves are very similar, −3.188 and −3.123 respectively.

Example 2

This example demonstrates the amplification and detection of CTX-M nucleic acid with probes and primers designed against locations 1, 2 and 3.

Figure 3:
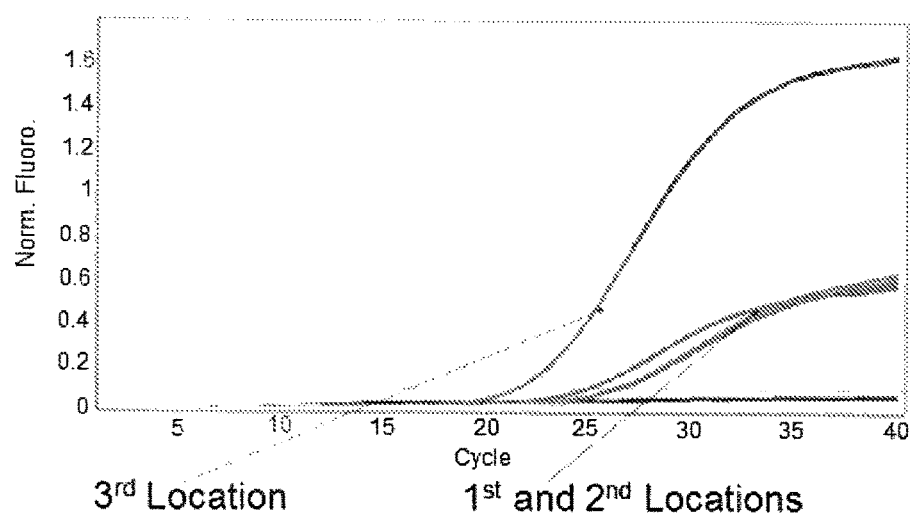
FIG. 3 shows the real-time detection of CTX-M15 nucleic acids with probes and primers designed for 3 different locations.

The primers and probes used are shown in Table 5 below. The amplification was performed similarly to that described in Example 1 and detection of CTX-M15 amplified nucleic acids is shown in FIG. 3. FIG. 3 shows the real-time detection of CTX-M15 nucleic acids with probes and primers designed for 3 different locations.

TABLE 5

| Location | Primer SEQ ID NO: | Probe SEQ ID NO: |
|---|---|---|
| 1 | 2, 3, 6, 7, and 8 | 4 and 9 |
| 2 | 13, 14, 16 and 17 | 18 |
| 3 | 20, 21, 24 and 25 | 26 and 27 |

Example 3

This example illustrates the performance of primers and probes of Example 1 to detect CTX-M nucleic acids extracted and quantified from 9 different isolates as measured by Ct. Table 6 shows the Cts of different isolates in different CTXM groups as determined by the procedure described in Example 1.

TABLE 6

| CTX-M group | Isolate Name | CTX-M Ct, no IC | CTX-M Ct, with IC | IC Ct |
|---|---|---|---|---|
| CTX-M 1 | Misc 336 | 15.28 | 15.27 | 24.58 |
| CTX-M 1 | Misc 337 | 14.71 | 15.03 | 24.58 |
| CTX-M 9 | Ecoli 254 | 15.43 | 15.49 | 24.56 |
| CTX-M 15 | A15 | 15.32 | 15.32 | 24.65 |
| CTX-M 15 | H15 | 16.34 | 16.43 | 24.63 |
| CTX-M 15 | CUMC 245 | 16.82 | 16.82 | 24.39 |
| CTX-M-14 (CTX-M 9 group homolog) | La14 | 16.36 | 16.23 | 24.36 |
| CTX-M-14 (CTX-M 9 group homolog) | Lo14 | 15.11 | 15.17 | 24.28 |
| CTX-M-14 (CTX-M 9 group homolog) | Misc 439 | 16.35 | 16.26 | 24.33 |

The results in Table 6 demonstrate the ability of primers and probes from Example 1 to detect CTX-M target nucleic acids from different isolates representing CTX-M1, 9 and 15.

REFERENCES CITED

The following documents and publications are hereby incorporated by reference.

U.S. and Foreign Patent Documents

EP Patent No. 1408366
PCT Patent Publication No.
WO 1999/37085
WO 2001/042505
WO 2003/023357
U.S. Patent Publication No.
2007-0048758
2012-0244535
2013-0261014 A1
U.S. Patent No.
U.S. Pat. No. 3,194,805
U.S. Pat. No. 3,128,179
U.S. Pat. No. 3,996,345
U.S. Pat. No. 4,351,760
U.S. Pat. No. 4,415,732
U.S. Pat. No. 4,458,066
U.S. Pat. No. 4,683,195
U.S. Pat. No. 4,739,044
U.S. Pat. No. 4,757,141
U.S. Pat. No. 4,965,188
U.S. Pat. No. 4,997,928
U.S. Pat. No. 5,187,288
U.S. Pat. No. 5,188,934
U.S. Pat. No. 5,227,487
U.S. Pat. No. 5,231,191
U.S. Pat. No. 5,248,782
U.S. Pat. No. 5,304,645
U.S. Pat. No. 5,419,966
U.S. Pat. No. 5,433,896
U.S. Pat. No. 5,442,045
U.S. Pat. No. 5,508,178
U.S. Pat. No. 5,512,677
U.S. Pat. No. 5,538,848
U.S. Pat. No. 5,556,959
U.S. Pat. No. 7,582,739.
U.S. Pat. No. 5,583,236
U.S. Pat. No. 5,585,481
U.S. Pat. No. 5,696,251
U.S. Pat. No. 5,736,626
U.S. Pat. No. 5,801,155
U.S. Pat. No. 5,808,044
U.S. Pat. No. 5,852,191
U.S. Pat. No. 5,942,610
U.S. Pat. No. 5,986,086
U.S. Pat. No. 6,020,481
U.S. Pat. No. 6,127,121
U.S. Pat. No. 6,162,931
U.S. Pat. No. 6,180,295
U.S. Pat. No. 6,221,604
U.S. Pat. No. 6,312,894
U.S. Pat. No. 6,653,473
U.S. Pat. No. 6,683,173
U.S. Pat. No. 6,699,975
U.S. Pat. No. 6,727,356
U.S. Pat. No. 6,790,945

U.S. Pat. No. 6,949,367
U.S. Pat. No. 7,045,610
U.S. Pat. No. 7,205,105
U.S. Pat. No. 7,319,022.
U.S. Pat. No. 7,381,818
U.S. Pat. No. 7,759,126
U.S. Pat. No. 7,767,834
U.S. Pat. No. 8,163,910.

Non-Patent References

Agrawal et al., Tetrahedron Letters, 31:1543-1546 (1990)
Ausubel, et al., CURRENT PROTOCOLS IN MOLECULAR BIOLOGY. John Wiley & Sons (1987, 1988, 1989, 1990, 1991, 1992, 1993, 1994, 1995, 1996);
Bolli et al., *Nucleic Acids Res.*, 24:4660-4667 (1996)
Bonnet R., Antimicrob Agents Chemother., 48:1-14 (2004).
Capaldi, et al., Nuc. Acids Res., 28:E21 (2000)
Dallenne et al., J Antimicrob Chemother. 65: 490-5 (2010)
Dreier et al., J Clin Microbiol. 43(9):4551-7(2005)
Eckstein, (ed.), Oligonucleotides and Analogues: A Practical Approach, IRL Press. Oxford (1991)
Gait (ed.), OLIGONUCLEOTIDE SYNTHESIS: A PRACTICAL APPROACH, IRL Press (1984); and Eckstein (ed.), OLIGONUCLEOTIDES AND ANALOGUES: A PRACTICAL APPROACH, IRL Press (1991).
Gait, Oligonucleotide Synthesis, IRL Press (1990)
Garrido et al., Microb Drug Resist., 20(4):301-4 (2014)
Giusti et al., PCR Methods and Applications, 2:223-227 (1993)
Hawkey P M and Jones A M) J Antimicrob Chemother. 64: i3-10 (2009)
Holten K B, Onusko E M (August 2000). "Appropriate prescribing of oral beta-lactam antibiotics". American Family Physician 62 (3): 611-20)
Hoorfar et al., J Clin Microbiol. 42(5): 1863-8 (2004)
Helldal et al., Clin Microbiol Infect., 19: E87-90 (2013)
Leistner et al., Infect Drug Resist. 7:57-62 (2014)
Liebana et al., Clin. Infect. Dis 56, 1030-1037 (2013),
McPherson et al., PCR Basics, 2000; and Rapid Cycle Real-time PCR Methods and Applications: Quantification, Wittwer et al. (eds.). Springer-Verlag (2004).
Mullis et al., *Cold Spring Harb. Symp. Quant. Biol.,* 51 Pt 1:263-273 (1986)
Nelson et al., Nuc. Acids Res., 17:7187-7194 (1989)
Niemz, A. et al Trends Biotechnol., 29: 240-50 (2011)
Onnberg et al., APMIS. 119(4-5):287-95 (2011)
Picard et al., J Clin Microbiol. 47(3):751-7 (2009)
Reddy et al., J. W., Pharmacol. Therap., 84:1-111 (1999)
Sambrook, Fritsch & Maniatis, MOLECULAR CLONING: A LABORATORY MANUAL, Second Edition, Cold Spring Harbor Laboratory Press (1989)
Sharma et al., Nuc. Acids Res., 19:3019 (1991)
Sproat et al., Nuc. Acids Res., 15:4837 (1987)
Users Manual Model 392 and 394 Polynucleotide Synthesizers, pages 6-1 through 6-22, Applied Biosystems, Part No. 901237 (1991)
Walker et al., Biopolymers, 44:323-334 (1997) Wemmer et al., Curr. Opin. Struct. Biol., 7:355-361 (1997);
Zimmer et al., U. Prog. Biophys. Molec. Bio., 47:31-112 (1986)
Zuckerman et al., Nuc. Acids Res., 15:5305-5321 (1987)

What is claimed is:

1. A method for detecting a CTX-M nucleic acid in a sample, comprising:
   (a) contacting a sample suspected of containing the CTX-M nucleic acid with at least one flap primer having the formula:

$$5'-[X]_p-Y-3' \qquad (I),$$

wherein X is a 5' portion of the flap primer that is non-complementary to the CTX-M nucleic acid and Y is a 3' portion of the flap primer that is substantially complementary to at least a portion of the CTX-M nucleic acid, X has a sequence that comprises AATAAATCATAA (SEQ ID NO: 51) or at least four consecutive bases of AATAAATCATAA (SEQ ID NO: 51), Y has a sequence that is substantially complementary to at least a portion of a sequence selected from the group consisting of SEQ ID NO: 1, 12, 19 or 29, and p is 0 or 1, to produce a mixture;
   (b) incubating the mixture of step (a) under conditions sufficient to amplify the CTX-M nucleic acid, thereby generating an amplified CTX-M nucleic acid; and
   (c) detecting the amplified CTX-M nucleic acid using a fluorescence-generating probe having a sequence with substantial identity to a sequence selected from the group consisting of SEQ ID NO: 4, 9, 10, 11, 18, 22, 26, 27, 28, 32, 35, 36, 37, 38, 39, 40, 41, 42, 43, 44, 45, and 46, wherein G* is guanine analogue 6- amino-1H-pyrazolo [3 ,4-d]pyrimidin-4(5H)-one, $R_a$ is independently selected from $(M)_a$-Fl and $(M)_a$-Q, $R_b$ is independently selected from $(M)_a$-Fl and $(M)_a$-Q, M is a minor groove binder, a is 0 or 1,Fl is a fluorophore with emission wavelength between about 400 and 900nm, and Q is a non-fluorescent quencher, wherein substitution of $R_a$ and $R_b$ allows quenching of fluorescence when the probe is unhybridized, and wherein the CTX-M nucleic acid is a CTX-M nucleic acid of group 1, 9 or 15.

2. The method of claim 1, wherein X and Y are each about 4 to about 30 nucleotides in length.

3. The method of claim 1, wherein the fluorescence-generating probe further comprises a minor groove binder.

4. The method of claim 1, wherein the flap primer has a sequence having substantial identity to a sequence selected from the group consisting of SEQ ID NO: 2, 3, 6, 7, 8, 13, 14, 16, 17, 20, 21, 24, 25, 30, 31, 33, and 34.

5. The method of claim 1, wherein the flap primer comprises a sequence that is complementary to more than one portion of the CTX-M nucleic acid.

6. The method of claim 1, wherein X is $[A-B]_m$ and Y is $[A-B]_n$, wherein A represents a sugar phosphate backbone, modified sugar phosphate backbone, locked nucleic acid backbone, or a combination thereof, B represents a nucleic acid base or a modified base, m and n are integers of from about 4 to about 30.

7. The method of claim 1, further comprising the step of amplifying a control nucleic acid.

8. The method of claim 7, wherein the control nucleic acid has a sequence with substantial identity to SEQ ID NO: 47.

9. The method of claim 7, wherein the step of amplifying a control nucleic acid comprises using a fluorescence-generating probe having substantial identity to SEQ ID NO: 50, wherein G* is guanine analogue 6-amino-1H-pyrazolo [3,4-d]pyrimidin-4(5H)-one, $R_a$ is independently selected from $(M)_a$-Fl and $(M)_a$-Q, $R_b$ is independently selected from $(M)_a$-Fl and $(M)_a$-Q, M is a minor groove binder, a is 0 or 1, Fl is a fluorophore with emission wavelength between about 400 and 900 nm, and Q is a non-fluorescent quencher, wherein substitution of $R_a$ and $R_b$ allows quenching of fluorescence when the probe is unhybridized.

10. The method of claim 7, wherein the step of amplifying a control nucleic acid comprises using one or more primers having substantial identity to a sequence that is SEQ ID NO: 48 or 49.

11. A method for detecting a CTX-M nucleic acid in a sample, comprising:
    (a) contacting a sample suspected of containing the CTX-M nucleic acid with at least one primer having a sequence with substantial identity to a sequence selected from the group consisting of SEQ ID NO: 2, 3, 6, 7, 8, 13, 14, 16, 17, 20, 21, 24, 25, 30, 31, 33, and 34, to produce a mixture;
    (b) incubating the mixture of step (a) under conditions sufficient to amplify the CTX-M nucleic acid, thereby generating an amplified CTX-M nucleic acid; and
    (c) detecting the amplified CTX-M nucleic acid, using a fluorescence-generating probe having a sequence with substantial identity to a sequence selected from the group consisting of SEQ ID NO: 4, 9, 10, 11, 18, 22, 26, 27, 28, 32, 35, 36, 37, 38, 39, 40, 41, 42, 43, 44, 45, and 46, wherein G* is guanine analogue 6-amino-1 H-pyrazolo[3,4-d] pyrimidin-4(5H)-one, $R_a$ is independently selected from (M)$_a$-Fl and (M)$_a$-Q, R$_b$ is independently selected from (M)$_a$-Fl and (M)$_a$-Q, M is a minor groove binder, a is 0 or 1, Fl is a fluorophore with emission wavelength between about 400 and 900 nm, and Q is a non-fluorescent quencher, wherein substitution of R$_a$ and R$_b$ allows quenching of fluorescence when the probe is unhybridized, and wherein the CTX-M nucleic acid is a CTX-M nucleic acid of group 1, 9 or 15.

12. The method of claim 11, further comprising the step of amplifying a control nucleic acid.

13. The method of claim 12, wherein the control nucleic acid has a sequence of SEQ ID NO: 47.

14. The method of claim 12, wherein the step of amplifying a control nucleic acid comprises using a fluorescence-generating probe having substantial identity to SEQ ID NO: 50, wherein G* is guanine analogue 6-amino-1H-pyrazolo[3,4-d]pyrimidin-4(5H)-one, R$_a$ is independently selected from (M)$_a$-Fl and (M)$_a$-Q, R$_b$ is independently selected from (M)$_a$-Fl and (M)$_a$-Q, M is a minor groove binder, a is 0 or 1, Fl is a fluorophore with emission wavelength between about 400 and 900 nm, and Q is a non-fluorescent quencher, wherein substitution of R$_a$ and R$_b$ allows quenching of fluorescence when the probe is unhybridized.

15. The method of claim 12, wherein the step of amplifying a control nucleic acid comprises using one or more primers having substantial identity to a sequence that is SEQ ID NO: 48 or 49.

16. A method for detecting a CTX-M nucleic acid in a sample, comprising:
   (a) contacting a sample suspected of containing the CTX-M nucleic acid with at least one flap primer having the formula:

5'-[X]$_p$-Y-3'   (I), wherein X is a 5' portion of the flap primer that is non-complementary to the CTX-M nucleic acid and Y is a 3' portion of the flap primer that is substantially complementary to at least a portion of the CTX-M nucleic acid, and p is 0 or 1, to produce a mixture;
   (b) incubating the mixture of step (a) under conditions sufficient to amplify the CTX-M nucleic acid, thereby generating an amplified CTX-M nucleic acid; and
   (c) detecting the amplified CTX-M nucleic acid using a fluorescence-generating probe having a sequence with substantial identity to a sequence selected from the group consisting of SEQ ID NO: 4, 9, 10, 11, 18, 22, 26, 27, 28, 32, 35, 36, 37, 38, 39, 40, 41, 42, 43, 44, 45, and 46, wherein G* is guanine analogue 6-amino-1H-pyrazolo[3,4-d]pyrimidin-4(5H)-one, R$_a$ is independently selected from (M)$_a$-Fl and (M)$_a$-Q, R$_b$ is independently selected from (M)$_a$-Fl and (M)$_a$-Q, M is a minor groove binder, a is 0 or 1, Fl is a fluorophore with emission wavelength between about 400 and 900 nm, and Q is a non-fluorescent quencher, wherein substitution of R$_a$ and R$_b$ allows quenching of fluorescence when the probe is unhybridized, and wherein the CTX-M nucleic acid is a CTX-M nucleic acid of group 1, 9 or 15.

17. The method of claim 16, wherein X has a sequence that comprises AATAAATCATAA (SEQ ID NO: 51) or at least four consecutive bases of AATAAATCATAA (SEQ ID NO: 51), and Y has a sequence that is substantially complementary to at least a portion of a sequence selected from the group consisting of SEQ ID NO: 1, 12, 19 or 29.

18. The method of claim 16, wherein the flap primer has a sequence with substantial identity to a sequence selected from the group consisting of SEQ ID NO: 2, 3, 6, 7, 8, 13, 14, 16, 17, 20, 21, 24, 25, 30, 31, 33, and 34.

19. The method of claim 16, further comprising the step of amplifying a control nucleic acid.

20. The method of claim 19, wherein the control nucleic acid has a sequence of SEQ ID NO: 47.

21. The method of claim 19, wherein the step of amplifying a control nucleic acid comprises using a fluorescence-generating probe having substantial identity to SEQ ID NO: 50, wherein G* is guanine analogue 6-amino-1H-pyrazolo[3,4-d]pyrimidin-4(5H)-one, Ra is independently selected from (M)a-Fl and (M)a-Q, Rb is independently selected from (M)a-Fl and (M)a-Q, M is a minor groove binder, a is 0 or 1, Fl is a fluorophore with emission wavelength between about 400 and 900 nm, and Q is a non-fluorescent quencher, wherein substitution of Ra and Rb allows quenching of fluorescence when the probe is unhybridized.

22. The method of claim 19, wherein the step of amplifying a control nucleic acid comprises using one or more primers having substantial identity to a sequence that is SEQ ID NO: 48 or 49.

23. A method for simultaneously detecting CTX-M groups 1 and 9 nucleic acids in a sample, comprising:
   (a) contacting a sample suspected of containing the CTX-M groups 1 and 9 nucleic acids with:
      (i) at least one forward flap primer comprising 5'-AATAAATCATAATCGGGTCGCCGGGAATG-3' (SEQ ID NO: 25), and
      (ii) at least one reverse flap primer comprising at least one of the following sequences: and
      5'-AATAAATCATGCGATGAGACGTTTCGTCTGGA-3' (SEQ ID NO:24), to produce a reaction mixture;
   (b) incubating the reaction mixture of step (a) under conditions sufficient to amplify the CTX-M groups 1 and 9 nucleic acids, thereby generating amplified CTX-M groups 1 and 9 nucleic acids; and
   (c) detecting the amplified CTX-M groups 1 and 9 nucleic acids.

24. The method of claim 23, wherein the step of detecting the amplified CTX-M groups 1 and 9 nucleic acids comprises using fluorescence-generating probes comprising at least one of the following sequences:

R$_a$-G*TCGGCTCGGTACGG-R$_b$,   (SEQ ID NO: 22)
   and
   R$_a$-G*TAGGTTCAGTGCGATCC-R$_b$,   (SEQ ID NO: 26)

wherein G* is guanine analogue 6-amino-1H-pyrazolo[3,4-d]pyrimidin-4(5H)-one, Ra is independently selected from (M)a-Fl and (M)a-Q, Rb is independently selected from (M)a-Fl and (M)a-Q, M is a minor groove binder, a is 0 or 1, Fl is a fluorophore with emission wavelength between about 400 and 900 nm, and Q is a non-fluorescent quencher, wherein substitution of Ra and Rb allows quenching of fluorescence when the probe is unhybridized.

25. The method of claim 23, further comprising the step of amplifying a control nucleic acid having a sequence of SEQ ID NO: 47.

26. The method of claim 25, wherein the step of amplifying a control nucleic acid comprises using a fluorescence-generating probe having substantial identity to SEQ ID NO: 50, wherein G* is guanine analogue 6-amino-1H-pyrazolo[3,4-d]pyrimidin-4(5H)-one, Ra is independently selected from (M)a-Fl and (M)a-Q, Rb is independently selected from (M)a-Fl and (M)a-Q, M is a minor groove binder, a is 0 or 1, Fl is a fluorophore with emission wavelength between about 400 and 900 nm, and Q is a non-fluorescent quencher, wherein substitution of Ra and Rb allows quenching of fluorescence when the probe is unhybridized.

27. The method of claim 25, wherein the step of amplifying a control nucleic acid comprises using one or more primers having substantial identity to a sequence that is SEQ ID NO: 48 or 49.

28. The method of claim 24, wherein the at least one forward flap primer further comprises 5'-AATAAATCATAAGCGGATCGCCCGGAAT-3' (SEQ ID NO: 21) and the at least one flap reverse primer further comprises 5'-AATAAATCATAAACGAAACGTTCCGTCTCGAC-3' (SEQ ID NO: 20).

\* \* \* \* \*

UNITED STATES PATENT AND TRADEMARK OFFICE
CERTIFICATE OF CORRECTION

| | | |
|---|---|---|
| PATENT NO. | : 10,266,903 B2 | Page 1 of 2 |
| APPLICATION NO. | : 14/957754 | |
| DATED | : April 23, 2019 | |
| INVENTOR(S) | : Irina A. Afonina et al. | |

It is certified that error appears in the above-identified patent and that said Letters Patent is hereby corrected as shown below:

On the Title Page
1. In Item (71), under "Applicant", in Column 1, Line 1, delete "ELITechGroup B.V.," and insert -- ELITechGroup, Inc., --, therefor.
2. On Page 2, in Item (56), under "OTHER PUBLICATIONS", in Column 1, Line 18, delete "β-actamases" and insert -- β-lactamases --, therefor.
3. On Page 2, in Item (56), under "OTHER PUBLICATIONS", in Column 2, Line 2, delete "Transcroption-PCR" and insert -- Transcription-PCR --, therefor.

In the Specification
4. In Column 1, Line 22, delete "monobactams" and insert -- monobactams, --, therefor.
5. In Column 3, Line 24, delete "CTX-M-13." and insert -- CTX-M-13, --, therefor.
6. In Column 3, Line 25, delete "(Bonnet." and insert -- (Bonnet, --, therefor.
7. In Column 4, Line 6, delete "urasil)" and insert -- uracil) --, therefor.
8. In Column 4, Line 22, delete "droxyprop-1-yny)l-" and insert -- droxyprop-1-ynyl)- --, therefor.
9. In Column 4, Line 28, delete "-d]pyrimidine." and insert -- -d]pyrimidine, --, therefor.
10. In Column 4, Line 34, delete "yny)-" and insert -- ynyl)- --, therefor.
11. In Column 4, Line 35, delete "-yny)-" and insert -- -ynyl)- --, therefor.
12. In Column 4, Line 50, delete "be find" and insert -- be found in --, therefor.
13. In Column 4, Line 59, delete "(522?," and insert -- (522), --, therefor.
14. In Column 4, Line 60, delete "(525)." and insert -- (525), --, therefor.
15. In Column 4, Line 62, delete "(533)." and insert -- (533), --, therefor.
16. In Column 4, Line 67, delete "Rhodamnine" and insert -- Rhodamine --, therefor.
17. In Column 7, Line 44, delete "70%." and insert -- 70%, --, therefor.
18. In Column 8, Line 41, delete "Green 1" and insert -- Green I --, therefor.
19. In Column 9, Line 13, delete "900 nm" and insert -- 900 nm, --, therefor.
20. In Column 11, Line 22, delete "embodiment 11" and insert -- embodiment Fl --, therefor.
21. In Column 12, Line 12, delete "-one." and insert -- -one, --, therefor.
22. In Column 12, Line 14, delete "NM is" and insert -- M is --, therefor.
23. In Column 12, Line 33, delete "Eclipse®," and insert -- Eclipse® --, therefor.
24. In Column 18, Line 21, delete "(I)." and insert -- (I), --, therefor.

Signed and Sealed this
Thirteenth Day of August, 2019

Andrei Iancu
*Director of the United States Patent and Trademark Office*

CERTIFICATE OF CORRECTION (continued)
U.S. Pat. No. 10,266,903 B2

25. In Column 19, Lines 5-6, delete "fluorphores," and insert -- fluorophores, --, therefor.
26. In Column 19, Line 26, delete "Biosystems." and insert -- Biosystems, --, therefor.
27. In Column 19, Line 28, delete "synthesis." and insert -- synthesis, --, therefor.
28. In Column 19, Line 29, delete "Gait." and insert -- Gait, --, therefor.
29. In Column 23, Line 4, delete "Probes." and insert -- Probes, --, therefor.
30. In Column 23, Line 29, delete "5-β-cyaoethyl-" and insert -- 5-β-cyanoethyl- --, therefor.
31. In Column 23, Line 52, delete "Polymerase." and insert -- Polymerase, --, therefor.
32. In Column 27, Line 14, delete "BIOLOGY." and insert -- BIOLOGY, --, therefor.
33. In Column 27, Line 22, delete "Press." and insert -- Press, --, therefor.
34. In Column 28, Line 7, delete "Dis 56," and insert -- Dis 56: --, therefor.

In the Claims
35. In Column 51, Lines 49-50, in Claim 1, delete "6- amino-1H-pyrazolo [3 ,4-d]pyrimidin-" and insert -- 6-amino-1H-pyrazolo [3,4-d]pyrimidin- --, therefor.
36. In Column 51, Line 54, in Claim 1, delete "900nm," and insert -- 900 nm, --, therefor.
37. In Column 52, Lines 66-67, in Claim 11, delete "6-amino-1 H-" and insert -- 6-amino-1H- --, therefor.
38. In Column 53, Line 1, in Claim 11, delete "-Fl" and insert -- -Fl --, therefor.
39. In Column 54, Line 2, in Claim 11, delete "-Fl" and insert -- -Fl --, therefor.
40. In Column 54, Lines 29-30, in Claim 23, delete "at least one reverse flap primer comprising at least one of the following sequences: and".

SEQUENCE LISTING

```
<160> NUMBER OF SEQ ID NOS: 52

<210> SEQ ID NO 1
<211> LENGTH: 54
<212> TYPE: DNA
<213> ORGANISM: Escherichia coli

<400> SEQUENCE: 1
ccaacgggcg cagctggtga cgtggatgaa aggcaatact accggtgcag cgag            54

<210> SEQ ID NO 2
<211> LENGTH: 30
<212> TYPE: DNA
<213> ORGANISM: Artificial Sequence
<220> FEATURE:
<223> OTHER INFORMATION: primer sequence CTX-E1
<220> FEATURE:
<221> NAME/KEY: m
<222> LOCATION: (27)..(27)
<223> OTHER INFORMATION: m is 3-(aminobutynyl)-1H-pyrazolo[3,4-d]
      pyrimidin-4(5H)-one

<400> SEQUENCE: 2
aataaatcat aactcgctgc accggtmgta                                      30

<210> SEQ ID NO 3
<211> LENGTH: 27
<212> TYPE: DNA
<213> ORGANISM: Artificial Sequence
<220> FEATURE:
<223> OTHER INFORMATION: primer sequence CTX-L1

<400> SEQUENCE: 3
```
aataaatcat aaccaacggg cgcagct                                          27

<210> SEQ ID NO 4
<211> LENGTH: 16
<212> TYPE: DNA
<213> ORGANISM: Artificial Sequence
<220> FEATURE:
<223> OTHER INFORMATION: probe sequence CTX-AP593-1
<220> FEATURE:
<221> NAME/KEY: m
<222> LOCATION: (1)..(1)
<223> OTHER INFORMATION: m is 6 amino 1H pyrazolo[3,4 d]pyrimidin 4(5H) one attached to minor groove binder and fluorophore or quencher
<220> FEATURE:
<221> NAME/KEY: m
<222> LOCATION: (6)..(6)
<223> OTHER INFORMATION: m is 3-(aminobutynyl)-1H-pyrazolo[3,4-d] pyrimidin-4(5H)-one
<220> FEATURE:
<221> NAME/KEY: m
<222> LOCATION: (16)..(16)
<223> OTHER INFORMATION: m is G attached to minor groove binder and fluorophore or quencher

<400> SEQUENCE: 4
mtgacmtgga tgaaam                                                      16

<210> SEQ ID NO 5
<211> LENGTH: 59
<212> TYPE: DNA
<213> ORGANISM: Escherichia coli

<400> SEQUENCE: 5
gaaacccagc gggcgcagtt ggtgacgtgg ctcaaaggca atacgaccgg cgcagccag       59

<210> SEQ ID NO 6
<211> LENGTH: 29
<212> TYPE: DNA
<213> ORGANISM: Artificial Sequence
<220> FEATURE:
<223> OTHER INFORMATION: primer sequence CTX-E2

<400> SEQUENCE: 6
aataaatcat aatggctgcg ccggtcgta                                        29

<210> SEQ ID NO 7
<211> LENGTH: 32
<212> TYPE: DNA
<213> ORGANISM: Artificial Sequence
<220> FEATURE:
<223> OTHER INFORMATION: primer sequence CTX-L2

<400> SEQUENCE: 7
aataaatcat aagaaaccca gcgggcgcag tt                                    32

<210> SEQ ID NO 8
<211> LENGTH: 27
<212> TYPE: DNA
<213> ORGANISM: Artificial Sequence
<220> FEATURE:
<223> OTHER INFORMATION: primer sequence CTX-L3

<400> SEQUENCE: 8
aataaatcat aaccagcggg cgcagtt                                          27

<210> SEQ ID NO 9
<211> LENGTH: 16

```
<212> TYPE: DNA
<213> ORGANISM: Artificial Sequence
<220> FEATURE:
<223> OTHER INFORMATION: probe sequence CTX-AP593-2
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (16)..(16)
<223> OTHER INFORMATION: m is G attached to minor groove binder and
      fluorophore or quencher

<400> SEQUENCE: 9
mtgacgtggc tcaaam                                                       16

<210> SEQ ID NO 10
<211> LENGTH: 18
<212> TYPE: DNA
<213> ORGANISM: Artificial Sequence
<220> FEATURE:
<223> OTHER INFORMATION: probe sequence CTX-AP593-7
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (6)..(6)
<223> OTHER INFORMATION: m is 3-(aminobutynyl)-1H-pyrazolo[3,4-d]
      pyrimidin-4(5H)-one
<220> FEATURE:
<221> NAME/KEY: m
<222> LOCATION: (10)..(10)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (18)..(18)
<223> OTHER INFORMATION: m is C attached to minor groove binder and
      fluorophore or quencher

<400> SEQUENCE: 10
mtgacmtggm tgaaaggm                                                     18

<210> SEQ ID NO 11
<211> LENGTH: 18
<212> TYPE: DNA
<213> ORGANISM: Artificial Sequence
<220> FEATURE:
<223> OTHER INFORMATION: probe sequence CTX-AP-8
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (18)..(18)
<223> OTHER INFORMATION: m is C attached to minor groove binder and
      fluorophore or quencher

<400> SEQUENCE: 11
mtgacgtggc tcaaaggm                                                     18

<210> SEQ ID NO 12
<211> LENGTH: 102
<212> TYPE: DNA
<213> ORGANISM: Escherichia coli
```

<400> SEQUENCE: 12
ccgaatctgt taaatcagcg agttgagatc aaaaaatctg accttgttaa ctataatccg         60
attgcggaaa agcacgtcaa tgggacgatg tcactggctg ag                          102

<210> SEQ ID NO 13
<211> LENGTH: 32
<212> TYPE: DNA
<213> ORGANISM: Artificial Sequence
<220> FEATURE:
<223> OTHER INFORMATION: primer sequence CTX-L5

<400> SEQUENCE: 13
aataaatcac tcagccagtg acatcgtccc at                                      32

<210> SEQ ID NO 14
<211> LENGTH: 34
<212> TYPE: DNA
<213> ORGANISM: Artificial Sequence
<220> FEATURE:
<223> OTHER INFORMATION: primer sequence CTX-E4
<220> FEATURE:
<221> NAME/KEY: m
<222> LOCATION: (28)..(28)
<223> OTHER INFORMATION: m is
      4-(4,6-Diamino-1H-pyrazolo[3,4-d]pyrimidin-3-yl)-but-3-yn-1-ol

<400> SEQUENCE: 14
aataaatcat accgaatctg ttaaatcmgc gagt                                    34

<210> SEQ ID NO 15
<211> LENGTH: 91
<212> TYPE: DNA
<213> ORGANISM: Escherichia coli

<400> SEQUENCE: 15
agctgcttaa tcagcctgtc gagatcaagc ctgccgatct ggttaactac aatccgattg         60
ccgaaaaaca cgtcaacggc acaatgacgc t                                       91

<210> SEQ ID NO 16
<211> LENGTH: 32
<212> TYPE: DNA
<213> ORGANISM: Artificial Sequence
<220> FEATURE:
<223> OTHER INFORMATION: primer sequence CTX-L4

<400> SEQUENCE: 16
aataaatcat aacgtcattg tgccgttgac gt                                      32

<210> SEQ ID NO 17
<211> LENGTH: 32
<212> TYPE: DNA
<213> ORGANISM: Artificial Sequence
<220> FEATURE:
<223> OTHER INFORMATION: primer sequence CTX-E3

<400> SEQUENCE: 17
aataaatcat agctgcttaa tcagcctgtc ga                                      32

<210> SEQ ID NO 18
<211> LENGTH: 16
<212> TYPE: DNA
<213> ORGANISM: Artificial Sequence
<220> FEATURE:
<223> OTHER INFORMATION: probe sequence CTX-AP593-3
<220> FEATURE:

```
<221> NAME/KEY: m
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (3)..(3)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (9)..(9)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (10)..(11)
<223> OTHER INFORMATION: m is 5-(4-hydroxy-but-1-ynyl)-1H-pyrimidine-2,
      4-dione
<220> FEATURE:
<221> NAME/KEY: m
<222> LOCATION: (12)..(12)
<223> OTHER INFORMATION: m is 3-(aminobutynyl)-1H-pyrazolo[3,4-d]
      pyrimidin-4(5H)-one
<220> FEATURE:
<221> NAME/KEY: m
<222> LOCATION: (16)..(16)
<223> OTHER INFORMATION: m is T attached to minor groove binder and
      fluorophore or quencher

<400> SEQUENCE: 18
mcmatcggmm mmtagm                                                      16

<210> SEQ ID NO 19
<211> LENGTH: 63
<212> TYPE: DNA
<213> ORGANISM: Escherichia coli

<400> SEQUENCE: 19
acgaaacgtt ccgtctcgac cgtaccgagc cgacgttaaa caccgccatt ccgggcgatc      60
cgc                                                                   63

<210> SEQ ID NO 20
<211> LENGTH: 32
<212> TYPE: DNA
<213> ORGANISM: Artificial Sequence
<220> FEATURE:
<223> OTHER INFORMATION: primer sequence CTX-E6

<400> SEQUENCE: 20
aataaatcat aaacgaaacg ttccgtctcg ac                                    32

<210> SEQ ID NO 21
<211> LENGTH: 29
<212> TYPE: DNA
<213> ORGANISM: Artificial Sequence
<220> FEATURE:
<223> OTHER INFORMATION: primer sequence CTX-L7

<400> SEQUENCE: 21
aataaatcat aagcggatcg cccggaatg                                        29

<210> SEQ ID NO 22
<211> LENGTH: 15
<212> TYPE: DNA
<213> ORGANISM: Artificial Sequence
<220> FEATURE:
<223> OTHER INFORMATION: probe sequence CTX-AP593-11
<220> FEATURE:
<221> NAME/KEY: m
```

```
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (15)..(15)
<223> OTHER INFORMATION: m is G attached to minor groove binder and
      fluorophore or quencher

<400> SEQUENCE: 22
mtcggctcgg tacgm                                                     15

<210> SEQ ID NO 23
<211> LENGTH: 71
<212> TYPE: DNA
<213> ORGANISM: Escherichia coli

<400> SEQUENCE: 23
gcgatgagac gtttcgtctg gatcgcactg aacctacgct gaataccgcc attcccggcg    60
acccgagaga c                                                         71

<210> SEQ ID NO 24
<211> LENGTH: 32
<212> TYPE: DNA
<213> ORGANISM: Artificial Sequence
<220> FEATURE:
<223> OTHER INFORMATION: primer sequence CTX-E5

<400> SEQUENCE: 24
aataaatcat gcgatgagac gtttcgtctg ga                                  32

<210> SEQ ID NO 25
<211> LENGTH: 29
<212> TYPE: DNA
<213> ORGANISM: Artificial Sequence
<220> FEATURE:
<223> OTHER INFORMATION: primer sequence CTX-L6

<400> SEQUENCE: 25
aataaatcat aatcgggtcg ccgggaatg                                      29

<210> SEQ ID NO 26
<211> LENGTH: 18
<212> TYPE: DNA
<213> ORGANISM: Artificial Sequence
<220> FEATURE:
<223> OTHER INFORMATION: probe sequence CTX-AP593-4
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (18)..(18)
<223> OTHER INFORMATION: m is C attached to minor groove binder and
      fluorophore or quencher

<400> SEQUENCE: 26
mtaggttcag tgcgatcm                                                  18

<210> SEQ ID NO 27
<211> LENGTH: 15
<212> TYPE: DNA
<213> ORGANISM: Artificial Sequence
<220> FEATURE:
<223> OTHER INFORMATION: probe sequence CTX-AP593-5
<220> FEATURE:
```

```
<221> NAME/KEY: m
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (15)..(15)
<223> OTHER INFORMATION: m is G attached to minor groove binder and
      fluorophore or quencher

<400> SEQUENCE: 27
mtcggctcgg tacgm                                                      15

<210> SEQ ID NO 28
<211> LENGTH: 18
<212> TYPE: DNA
<213> ORGANISM: Artificial Sequence
<220> FEATURE:
<223> OTHER INFORMATION: probe sequence CTX-AP593-10
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (18)..(18)
<223> OTHER INFORMATION: m is C attached to minor groove binder and
      fluorophore or quencher

<400> SEQUENCE: 28
mtaggttcag tgcgatcm                                                   18

<210> SEQ ID NO 29
<211> LENGTH: 90
<212> TYPE: DNA
<213> ORGANISM: Escherichia coli

<400> SEQUENCE: 29
acgtcaacgg cacaatgacg ctggcagaac tgagcgcggc cgcgttgcag tacagcgaca     60
ataccgccat gaacaaattg attgcccagc                                      90

<210> SEQ ID NO 30
<211> LENGTH: 32
<212> TYPE: DNA
<213> ORGANISM: Artificial Sequence
<220> FEATURE:
<223> OTHER INFORMATION: primer sequence CTX-L8

<400> SEQUENCE: 30
atcataacgt gagcaatcag cttattcatc gc                                   32

<210> SEQ ID NO 31
<211> LENGTH: 32
<212> TYPE: DNA
<213> ORGANISM: Artificial Sequence
<220> FEATURE:
<223> OTHER INFORMATION: primer sequence CTXM-E7

<400> SEQUENCE: 31
ataaatcata acgtcaacgg cacaatgacg ct                                   32

<210> SEQ ID NO 32
<211> LENGTH: 18
<212> TYPE: DNA
<213> ORGANISM: Artificial Sequence
<220> FEATURE:
<223> OTHER INFORMATION: probe sequence CTX-AP593-6
```

```
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (2)..(3)
<223> OTHER INFORMATION: m is 5-(4-hydroxy-but-1-ynyl)-1H-pyrimidine-2,
      4-dione
<220> FEATURE:
<221> NAME/KEY: m
<222> LOCATION: (4)..(4)
<223> OTHER INFORMATION: m is 3-(aminobutynyl)-1H-pyrazolo[3,4-d]
      pyrimidin-4(5H)-one
<220> FEATURE:
<221> NAME/KEY: m
<222> LOCATION: (12)..(12)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (18)..(18)
<223> OTHER INFORMATION: m is G attached to minor groove binder and
      fluorophore or quencher

<400> SEQUENCE: 32
mmmmtcgctg tmctgtag                                                  18

<210> SEQ ID NO 33
<211> LENGTH: 32
<212> TYPE: DNA
<213> ORGANISM: Artificial Sequence
<220> FEATURE:
<223> OTHER INFORMATION: primer sequence CTX-L9

<400> SEQUENCE: 33
atcataagct gggcaatcaa tttgttcatg gc                                  32

<210> SEQ ID NO 34
<211> LENGTH: 32
<212> TYPE: DNA
<213> ORGANISM: Artificial Sequence
<220> FEATURE:
<223> OTHER INFORMATION: primer sequence CTXM-E8

<400> SEQUENCE: 34
ataaatcata acgtcaacgg cacaatgacg ct                                  32

<210> SEQ ID NO 35
<211> LENGTH: 18
<212> TYPE: DNA
<213> ORGANISM: Artificial Sequence
<220> FEATURE:
<223> OTHER INFORMATION: primer sequence CTX-AP593-12
<220> FEATURE:
<221> NAME/KEY: m
<222> LOCATION: (1)..(1)
<223> OTHER INFORMATION: m is G attached to minor groove binder and
      fluorophore or quencher
<220> FEATURE:
<221> NAME/KEY: m
<222> LOCATION: (4)..(4)
<223> OTHER INFORMATION: m is 3-(aminobutynyl)-1H-pyrazolo[3,4-d]
      pyrimidin-4(5H)-one
<220> FEATURE:
<221> NAME/KEY: m
<222> LOCATION: (17)..(17)
<223> OTHER INFORMATION: m is
      4-(4,6-Diamino-1H-pyrazolo[3,4-d]pyrimidin-3-yl)-but-3-yn-1-ol
<220> FEATURE:
<221> NAME/KEY: m
<222> LOCATION: (18)..(18)
```

<223> OTHER INFORMATION: m is G attached to minor groove binder and
       fluorophore or quencher

<400> SEQUENCE: 35
mttmtcgctg tactgtmm                                                    18

<210> SEQ ID NO 36
<211> LENGTH: 17
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)
<223> OTHER INFORMATION: m is A attached to minor groove binder and
       fluorophore or quencher
<220> FEATURE:
<221> NAME/KEY: m
<222> LOCATION: (17)..(17)
<223> OTHER INFORMATION: m is T attached to minor groove binder and
       fluorophore or quencher

<400> SEQUENCE: 36
mtggtgacaa agagagm                                                     17

<210> SEQ ID NO 37
<211> LENGTH: 17
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)
<223> OTHER INFORMATION: m is C attached to minor groove binder and
       fluorophore or quencher
<220> FEATURE:
<221> NAME/KEY: m
<222> LOCATION: (17)..(17)
<223> OTHER INFORMATION: m is T attached to minor groove binder and
       fluorophore or quencher

<400> SEQUENCE: 37
mcgcgaacat catccgm                                                     17

<210> SEQ ID NO 38
<211> LENGTH: 15
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)
<223> OTHER INFORMATION: m is C attached to minor groove binder and
       fluorophore or quencher
<220> FEATURE:
<221> NAME/KEY: m
<222> LOCATION: (15)..(15)
<223> OTHER INFORMATION: m is C attached to minor groove binder and
       fluorophore or quencher

<400> SEQUENCE: 38
mggcggcgtg cattm                                                       15

<210> SEQ ID NO 39
<211> LENGTH: 14
<212> TYPE: DNA
<213> ORGANISM: Artificial Sequence
<220> FEATURE:

<223> OTHER INFORMATION: probe sequence
<220> FEATURE:
<221> NAME/KEY: m
<222> LOCATION: (1)..(1)
<223> OTHER INFORMATION: m is G attached to minor groove binder and
      fluorophore or quencher
<220> FEATURE:
<221> NAME/KEY: m
<222> LOCATION: (14)..(14)
<223> OTHER INFORMATION: m is G attached to minor groove binder and
      fluorophore or quencher

<400> SEQUENCE: 39
mcccagcagc agcm                                                         14

<210> SEQ ID NO 40
<211> LENGTH: 14
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)
<223> OTHER INFORMATION: m is C attached to minor groove binder and
      fluorophore or quencher
<220> FEATURE:
<221> NAME/KEY: m
<222> LOCATION: (14)..(14)
<223> OTHER INFORMATION: m is A attached to minor groove binder and
      fluorophore or quencher

<400> SEQUENCE: 40
mccgggaggc gtgm                                                         14

<210> SEQ ID NO 41
<211> LENGTH: 14
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)
<223> OTHER INFORMATION: m is G attached to minor groove binder and
      fluorophore or quencher
<220> FEATURE:
<221> NAME/KEY: m
<222> LOCATION: (14)..(14)
<223> OTHER INFORMATION: m is A attached to minor groove binder and
      fluorophore or quencher

<400> SEQUENCE: 41
matcgcgcgg gcam                                                         14

<210> SEQ ID NO 42
<211> LENGTH: 16
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)
<223> OTHER INFORMATION: m is T attached to minor groove binder and
      fluorophore or quencher
<220> FEATURE:
<221> NAME/KEY: m
<222> LOCATION: (16)..(16)
<223> OTHER INFORMATION: m is A attached to minor groove binder and
      fluorophore or quencher

<400> SEQUENCE: 42

```
mcatgcgctg ggcgam                                                   16
```

<210> SEQ ID NO 43
<211> LENGTH: 18
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)
<223> OTHER INFORMATION: m is A attached to minor groove binder and
      fluorophore or quencher
<220> FEATURE:
<221> NAME/KEY: m
<222> LOCATION: (18)..(18)
<223> OTHER INFORMATION: m is G attached to minor groove binder and
      fluorophore or quencher

<400> SEQUENCE: 43

```
mgcttacgct gggtcatm                                                 18
```

<210> SEQ ID NO 44
<211> LENGTH: 17
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)
<223> OTHER INFORMATION: m is G attached to minor groove binder and
      fluorophore or quencher
<220> FEATURE:
<221> NAME/KEY: m
<222> LOCATION: (17)..(17)
<223> OTHER INFORMATION: m is T attached to minor groove binder and
      fluorophore or quencher

<400> SEQUENCE: 44

```
magccacgtc accaacm                                                  17
```

<210> SEQ ID NO 45
<211> LENGTH: 15
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)
<223> OTHER INFORMATION: m is G attached to minor groove binder and
      fluorophore or quencher
<220> FEATURE:
<221> NAME/KEY: m
<222> LOCATION: (15)..(15)
<223> OTHER INFORMATION: m is A attached to minor groove binder and
      fluorophore or quencher

<400> SEQUENCE: 45

```
mgtgatctgg ccgcm                                                    15
```

<210> SEQ ID NO 46
<211> LENGTH: 12
<212> TYPE: DNA
<213> ORGANISM: Artificial Sequence
<220> FEATURE:
<223> OTHER INFORMATION: probe sequence
<220> FEATURE:
<221> NAME/KEY: m
<222> LOCATION: (1)..(1)

```
<223> OTHER INFORMATION: m is G attached to minor groove binder and
      fluorophore or quencher
<220> FEATURE:
<221> NAME/KEY: m
<222> LOCATION: (12)..(12)
<223> OTHER INFORMATION: m is C attached to minor groove binder and
      fluorophore or quencher

<400> SEQUENCE: 46
mgcgcacgac cm                                                             12

<210> SEQ ID NO 47
<211> LENGTH: 68
<212> TYPE: DNA
<213> ORGANISM: Artificial Sequence
<220> FEATURE:
<223> OTHER INFORMATION: internal control sequence

<400> SEQUENCE: 47
ctgcacggac cagttacttt acggaccacg taccgcattg gtacaagatc tccggtagaa         60
aaaatgag                                                                  68

<210> SEQ ID NO 48
<211> LENGTH: 23
<212> TYPE: DNA
<213> ORGANISM: Artificial Sequence
<220> FEATURE:
<223> OTHER INFORMATION: primer sequence E6132-L

<400> SEQUENCE: 48
ctgcacggac cagttacttt acg                                                 23

<210> SEQ ID NO 49
<211> LENGTH: 26
<212> TYPE: DNA
<213> ORGANISM: Artificial Sequence
<220> FEATURE:
<223> OTHER INFORMATION: primer sequence E6132-E

<400> SEQUENCE: 49 ctcattttt ctaccggaga tcttgt                                               26

<210> SEQ ID NO 50
<211> LENGTH: 17
<212> TYPE: DNA
<213> ORGANISM: Artificial Sequence
<220> FEATURE:
<223> OTHER INFORMATION: probe sequence D6132-AP525-TM3
<220> FEATURE:
<221> NAME/KEY: m
<222> LOCATION: (1)..(1)
<223> OTHER INFORMATION: m is 6 amino 1H pyrazolo[3,4 d]pyrimidin 4(5H)
      one attached to minor groove binder and fluorophore or quencher
<220> FEATURE:
<221> NAME/KEY: m
<222> LOCATION: (17)..(17)
<223> OTHER INFORMATION: m is G attached to minor groove binder and
      fluorophore or quencher

<400> SEQUENCE: 50
maccacgtac cgcattm                                                        17

<210> SEQ ID NO 51
<211> LENGTH: 12
<212> TYPE: DNA
<213> ORGANISM: Artificial Sequence
<220> FEATURE:
<223> OTHER INFORMATION: primer flap sequence
```

```
<400> SEQUENCE: 51
aataaatcat aa                                                    12

<210> SEQ ID NO 52
<211> LENGTH: 12
<212> TYPE: DNA
<213> ORGANISM: Artificial Sequence
<220> FEATURE:
<223> OTHER INFORMATION: general flap primer sequence
<220> FEATURE:
<221> NAME/KEY: m
<222> LOCATION: (12)..(12)
<223> OTHER INFORMATION: m is A attached to oligonucleotide sequence

<400> SEQUENCE: 52
aataaatcat am                                                    12
```